United States Patent
Thrippleton et al.

(10) Patent No.: US 8,440,424 B2
(45) Date of Patent: May 14, 2013

(54) IDENTIFICATION OF ANTIBIOTIC RESISTANCE USING LABELLED ANTIBIOTICS

(75) Inventors: Ian Thrippleton, Düsseldorf (DE); Walter von Freiherr Stein, Düsseldorf (DE)

(73) Assignee: miacom Diagnostics GmbH, Duesseldorf (DE)

( * ) Notice: Subject to any disclaimer, the term of this patent is extended or adjusted under 35 U.S.C. 154(b) by 122 days.

(21) Appl. No.: 12/865,769

(22) PCT Filed: Jan. 30, 2009

(86) PCT No.: PCT/EP2009/000621
§ 371 (c)(1), (2), (4) Date: Aug. 31, 2010

(87) PCT Pub. No.: WO2009/095258
PCT Pub. Date: Aug. 6, 2009

(65) Prior Publication Data
US 2011/0003306 A1 Jan. 6, 2011

(30) Foreign Application Priority Data
Feb. 1, 2008 (EP) .................................. 08001947.0

(51) Int. Cl.
*C12Q 1/02* (2006.01)
(52) U.S. Cl.
USPC .......................................................... 435/29
(58) Field of Classification Search ........................ None
See application file for complete search history.

(56) References Cited

PUBLICATIONS

Tiyanont et al. (PNAS, 103:11033-11038, 2006).*
Jarzembowski et al. (Curr. Microbiol., 57:167-169, published online Jun. 24, 2008).*
Daniel Richard A et al: "Control of cell morphogenesis in bacteria: two distinct ways to make a rod-shaped cell." Cell Jun. 13, 2003, vol. 11 3, No. 6, Jun. 13, 2003, pp. 767-776, XP002526980 ISSN: 0092-8674.
Tiyanont Kittichoat et al: "Imaging peptidoglycan biosynthesis in *Bacillus subtilis* with fluorescent antibiotics." Proceedings of the National Academy of Sciences of the United States of America Jul. 18, 2006, vol. 103, No. 29, Jul. 18, 2006, pp. 11 033-1 1038, XP002526981 ISSN: 0027-8424.
Ball P R et al: "Plasmid Mediated Tetracycline Resistance in *Escherichia coli* Involves Increased Efflux of the Antibiotic" Biochemical and Biophysical Research Communications, vol. 93, No. 1, 1980, pp. 74-81, XP009116593 ISSN: 0006-291X.
Database Biosis [Online] Biosciences Information Service, Philadelphia, PA, US; Apr. 2004, Kao J C et al: "Transscleral permeability of fluorescent-labelled antibiotics" XP002526983 Database accession No. PREV200510252823.
Yamada T et al: "tRNA binding to programmed ribosomes increases the ribosomal affinity for tuberactinomycin 0" FEBS Letters, Elsevier, Amsterdam, NL, vol. 179, No. 1, Jan. 1, 1985, pp. 37-40, XP025597742 ISSN: 001 4-5793 [retrieved on Jan. 11, 1985].

* cited by examiner

*Primary Examiner* — Brian J Gangle
(74) *Attorney, Agent, or Firm* — Rothwell, Figg, Ernst & Manbeck, P.C.

(57) ABSTRACT

Subject of the present invention is a method for detection of an antibiotic resistance in a micro-organism comprising the steps of exposing suspected micro-organism to a labelled (fluorescent) antibiotic and observing the differences between it and a non-resistant micro-organism of the same type.

28 Claims, No Drawings

IDENTIFICATION OF ANTIBIOTIC RESISTANCE USING LABELLED ANTIBIOTICS

CROSS REFERENCE TO RELATED APPLICATION

This application is a 35 U.S.C. 371 National Phase Entry Application from PCT/EP2009/000621, filed Jan. 30, 2009, which claims the benefit of European Patent Application No. 08001949 filed on Feb. 1, 2008, the disclosure of which is incorporated herein in its entirety by reference.

Subject of the present invention is a method for detection of an antibiotic resistance in a micro-organism.

The characterisation of micro-organisms in routine diagnostic procedures encompasses the determination of a species' identity and its sensitivity towards antibiotics. In order to achieve this, micro-organisms need to be taken from their environment and enriched in a selective environment for the separate identification (ID) and antibiotic sensitivity testing (AST). Currently the AST/ID of micro-organisms is achieved by identifying presence or absence of an array of biochemical features and the (non-) capability to grow in the presence of antibiotics. Alternatively DNA can be extracted from a sample and the then pooled DNA is tested for the presence/absence of specific sequences utilising gene amplification techniques. This can signal the presence of an organism in the sample. Equally, the presence of a gene coding for antibiotic resistance in the sample can be detected. By definition, extracting DNA directly from a sample renders pooled DNA from an unknown mixture of cells. Unequivocal results can only be achieved if the DNA is extracted from a pure colony.

Staphylococcus aureus is one of the most common causes of nosocomial or community-based infections, leading to serious illnesses with high rates of morbidity and mortality. In recent years, the increase in the number of bacterial strains that show resistance to methicillin-resistant Staphylococcus aureus (MRSA) has become a serious clinical and epidemiological problem because this antibiotic (or analogue) is considered the first option in the treatment of staphylococci infections. The resistance to this antibiotic implies resistance to all β-lactam antibiotics. For these reasons, accuracy and promptness in the detection of methicillin resistance is of key importance to ensure correct antibiotic treatment in infected patients as well as control of MRSA isolates in hospital environments, to avoid them spreading.

MRSA strains harbour the mecA gene, which encodes a modified PBP2 protein (PBP2' or PBP2a) with low affinity for methicillin and all β-lactam antibiotics. Phenotypic expression of methicillin resistance may alter depending on the growth conditions for S. aureus, such as temperature or osmolarity of the medium, and this may affect the accuracy of the methods used to detect methicillin resistance (1). Heteroresistant bacterial strains may evolve into fully resistant strains and therefore be selected in those patients receiving β-lactam antibiotics, thus causing therapeutic failure. From a clinical point of view they should, therefore, be considered fully resistant.

There are several methods for detecting methicillin resistance (1,9) including classical methods for determining a minimum inhibitory concentration MIC (disc diffusion, Etest, or broth dilution), screening techniques with solid culture medium containing oxacillin, and methods that detect the mecA gene or its protein product (PBP2' protein) (3,4). Detection of the mecA gene is considered as the reference method for determining resistance to methicillin (1). However, many laboratories throughout the world do not have the funds required, the capacity or the experienced staff required to provide molecular assays for detecting MRSA isolates. It is therefore essential that other, more useful, screening methods are incorporated into routine clinical practice. Moreover, the presence of antibiotic resistance has it's relevance at several levels, all of which are of clinical significance 1. Presence of a gene conveying resistance, such as mecA, mef(E),
2. Presence of a repressor gene inhibiting the phenotypic expression of said resistance mechanism; e.g. MecA repressor
3. Multiple resistance mechanisms; e.g. Macrolide resistance via modification of the ribosomal binding site and presence of efflux mechanism(s).
4. Level of expression of said resistance mechanism regulated via transcription and translation detectable as the phenotype Current cultural techniques require the isolation of a discrete colony and the subsequent identification and resistance testing, assuming that a single colony is derived from a single cell and is therefore deemed to be pure. In reality however, the generation of a pure colony from a clinical sample, where pathogens frequently live in bio-film communities, cannot be guaranteed. Equally, using amplification technologies, nucleic acid sequences from multiple cells are extracted and amplified and can therefore render false positive results. Only if identification and resistance can be performed and be read on individual cells, is it possible to a true picture of the invading pathogen.

A wide range of antibiotics carry a primary amino group. It is well known in the art that reagents such as Fluorescein-isothiocyanate (FITC), Fluorecein-N-hydroxysuccinimide ester will readily react with said primary amines.

The increasing spread of antibiotic resistance in both community and healthcare systems necessitates the precision and speed of molecular biology. However, the complexity and cost of these assays prohibits the widespread application in a routine testing environment.

Taking into account the difficulties in identifying a micro-organism and its potential resistance against an antibiotic in a biological sample, it is desirable to be able to quickly identify a pathogen directly from a sample without culturing and without amplification and in addition to be able to detect or exclude the presence of resistance towards an antibiotic of choice.

It is the intention of this invention to provide a solution by enabling the simultaneous identification and resistance testing on the cellular level. This reduces the complexity of the assays so that an unambiguous assignment of a phenotype can be made for individual cells. The assays are designed to reduce handling and turnaround time to enable screening programmes such as the screening of all incoming patients for e.g. MRSA.

A first subject of the present invention is thus a method for the detection of an antibiotic resistance in a predetermined micro-organism in a biological sample, comprising the steps:
(a) providing a labelled antibiotic,
(b) contacting the labelled antibiotic with a biological sample comprising the micro-organism under conditions which allow binding of the labeled antibiotic to its binding site in the micro-organism,
(c) detecting the labelled antibiotic in the micro-organism, and
(d) identifying a micro-organism in which the amount of detectable label is altered with respect to the amount of detectable label in the predetermined micro-organism in its non-resistant form, wherein microorganisms identified in step (d) are microorganism resistant against the antibiotic.

The underlying principle of the method is that if an organism is sensitive or resistant to an antibiotic, it will markedly differ from its resistant or sensitive counterpart. The antibiotics may bind to their respective binding sites either in the cell lumen, cytoplasm, the cell wall or to secreted proteins such as beta-lactamases. Depending upon the resistance mechanism, resistant organisms may mostly show either reduced or no affinity to the antibiotic due to reduced affinity to e.g. ribosomes or penicillin binding proteins. Conversely, if the resistance mechanism is due to the ab/adsorption to the outer cell membrane, the resistant organism will exhibit highly enhanced fluorescence.

The biological sample may be any sample of biological origin, such as a clinical or food sample, suspected of comprising an antibiotic-resistant microorganism. The micro-organism may be selected from the group consisting of bacteria, yeasts and moulds, in particular from Gram positive and Gram negative bacteria.

Preferably, the predetermined micro-organism is selected from the group consisting of *Staphylococcus, Enterococcus,* and *Streptococcus.*

More preferably, the predetermined micro-organism is selected from the group consisting of Methicillin resistant *Staphylococcus,* Vancomycin resistant *Staphylococcus, Vancomycin* resistant *Enterococcus,* and high level Aminoglycoside resistant Enterococci.

The microrganism is even more preferably selected from the group consisting of *Staphylococcus aureus,* Methicillin Resistant *Staphylococcus aureus* (MRSA), Vancomycin Resistant *Staphylococcus aureus* (VRSA), Vancomycin Resistant *Staphylococcus* (VRS), Vancomycin Resistant Enterococci (VRE), *Streptococcus pneumoniae,* drug resistant *Streptococcus pneumoniae* (DRSP), and Aminoglycoside resistant Enterococci (HLAR).

The antibiotic to be provided in step (a) may be any antibiotic. Preferably, the antibiotic is selected from the group consisting of aminoglycosides, carbacephems, carbapenems, cephalosporins, glycopeptides, macrolides, monobactams, beta-lactam antibiotics, quinolones, bacitracin, sulfonamides, tetracyclines, streptogramines, chloramphenicol, clindamycin, and lincosamide.

More preferably, the antibiotics are selected from beta-lactam antibiotics, macrolides, lincosamide, and streptogramins.

Even more preferably, the antibiotic is selected from the group consisting of Amikacin, Gentamicin, Kanamycin, Neomycin, Netilmicin, Streptomycin, Tobramycin, Loracarbef, Ertapenem, Imipenem, Cilastatin, Meropenem, Cefadroxil, Cefazolin, Cephalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefsulodine, Cefepime, Teicoplanin, Vancomycin, Azithromycin, Clarithromycin, Dirithromycin, Erythromycin, Roxithromycin, Troleandomycin, Aztreonam, Amoxicillin, Ampicillin, Azlocillin, Carbenicillin, Cloxacillin, Dicloxacillin, Flucloxacillin, Mezlocillin, Nafcillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Mafenide, Prontosil, Sulfacetamide, Sulfamethizole, Sulfanilimide, Sulfasalazine, Sulfisoxazole, Trimethoprim, Trimethoprim sulfa, Sulfamethoxazole, Co-trimoxazole, Demeclocycline, Doxycycline, Minocycline, Oxytetracycline, Tetracycline, Chloramphenicol, Clindamycin, Ethambutol, Fosfomycin, Furazolidone, Isoniazid, Linezolid, Metronidazole, Mupirocin, Nitrofurantoin, Platensimycin, Pyrazinamide, Quinupristin/Dalfopristin, Rifampin, Spectinomycin, Amphotericin B, Flucanazole, Fluoropyrimidins, Gentamycin, and clavulanic acid.

Most preferably, the antibiotic is selected from Vancomycin, Methicillin, Clindamycin, Trimethoprim, Trimethoprim sulfa, Gentamycin, and clavulanic acid.

Surprisingly, a modification of an antibiotic with a labelling group does not hinder the binding of an antibiotic to its binding site in the micro-organism.

Preferably, the antibiotic is labelled by a luminescent labelling group. Many fluorophores suitable as labelling groups in the present invention are available. The labelling group may be selected to fit the filters present in the market. The antibiotic may be labelled by any suitable labelling group which can be detected in a micro-organism. Preferably, the labelling group is a fluorescent labelling group. More preferably, the labelling group is selected from Fluorescein and Atto-495-NSI.

The labelling group may be coupled to the antibiotic at a functional group. A wide range of antibiotics carry a primary amino group. For example, a fluorescent compound such as Fluoresceinisothiocyanate (FITC), Fluorecein-N-hydroxysuccinimide ester may be reacted with an amino group of an antibiotic, resulting in a Fluorescein-labelled antibiotic. Other antibiotics such as Clindamycin carry a thio-methyl group which can be coupled to a labelling group. Conditions were found to mildly substitute the methyl group of Clindamycin with a spacer molecule forming a dithio bridge.

The labelling group may be coupled to the antibiotic via a spacer. Many spacers are known in the art and may be applied. Using protein chemistry techniques well known in the art many ways of attaching a spacer and subsequently attaching a fluorophor are feasible. In a preferred embodiment cysteine is chosen as its primary amino group may readily be labelled with a fluorophor. Molecules with longer carbon backbones and other reactive groups well known in the art may also be chosen as linker/spacer between any fluorophor and an antibiotic substance.

A list of antibiotics modified with a fluorophor with or without a spacer is compiled in Table 1. It is preferred that the antibiotics (in particular of Table 1) are labelled with Fluorescein or Atto-495-NSI.

In order to combine the identification with the resistance status, the conditions which allow binding of the labelled antibiotic to its binding site in the micro-organism in step (b) may refer to a binding assay which is not inhibited by the in-situ hybridisation procedure, enabling either a concomitant or subsequent determination of both identification and resistance status in individual cells and cell populations.

A preferred binding site is the PBP2 protein (Penicillin Binding Protein) in *Staphylococcus* encoded by the mecA gene. In *Staphylococcus* resistant against beta-lactam antibiotics, the mecA gene encodes a modified PBP2 protein (PBP2' or PBP2a) with low affinity for methicillin and all β-lactam antibiotics. Thus, in a more preferred embodiment, the micro-organism is a MRSA strain harbour the mecA gene, which encodes a modified PBP2 protein (PBP2' or PBP2a) with low affinity for methicillin and all β-lactam antibiotics, and the antibiotic is a beta-lactam antibiotic.

A further preferred application is for the determination of resistance due to point mutations in the 23s ribosomal RNA. The point mutations at different position induce resistance to a wide array of antibiotics such as Macrolides, Ketolides, Tetracyclin, Thiazolantibiotics, Lincosamin, Chloramphenicol, Streptogramin, Amecitin, Animosycin, Sparsoycin and Puromycin. Detailed effects of respective point mutations are listed in Table 3. Point mutations at different positions of the 23S rRNA can generate an iso-phenotype. It would require an array of oligo-nucleotide probes to cover all possibilities. This invention offers a cost effective and efficient way of detecting antibiotic resistance irrespective of the position of the mutation.

Another preferred application is the detection of the binding of Vancomycin to surface proteins of *Staphylococcus aureus* which are anchored to the cell wall peptidoglycan. Vancomycin resistant Staphylococci bind the antibiotic to such an extent that it renders Vancomycin ineffective. Labelled Vancomycin therefore will preferably bind to resistant organisms.

In the present invention, the amount of detectable label in the micro-organism corresponds to the signal of the labelling group of the antibiotic. The amount of detectable label may be directly proportional to the signal obtained from the labeling group.

The method of the present invention may comprise steps to remove labelling groups which have been cleaved off from the antibiotic or/and to remove labelled antibiotic which is not bound to a micro-organism. Such steps may improve the signal-to-noise ratio.

In step (c) of the method of the present invention, the label may be detected by any suitable method known in the art. The reading of the assay may require a resolution down to the individual cell. Preferably, the label is detected via epifluorescence microscopy, flow cytometry, laser scanning devices, time resolved fluorometry, luminescence detection, isotope detection, hyper spectral imaging scanner, Surface Plasmon Resonance or/and another evanscesence based reading technology.

In step (d) of the method of the present invention, alteration of the amount of detectable label may be an increase of detectable label or a decrease of detectable label. In the method of the present invention, the antibiotic resistance to be detected is predetermined by the provision of a labelled antibiotic in step (a). Table 4 indicates resistance mechanisms against commonly known antibiotics in clinically relevant micro-organisms. From the resistance mechanism of a particular predetermined micro-organism, such as indicated in Table 4, is can be deduced which combination of microorganism/antibiotic resistance are expected to show an increased amount of detectable label in antibiotic resistant cells, and which combination shows a decreased amount of detectable label. For instance, a decrease of the amount of detectable label is expected in micro-organisms resistant against β-lactam antibiotics or macrolides, such as MSRA, ORSA, etc. An increased amount of detectable label is expected in VRSA. A decrease of detectable label is expected in Vancomycin resistant Enterococci, due to the different resistance mechanism as in VRSA. Further details can be found in Table 4.

In the present invention, the predetermined microorganism in its non-resistant form can be employed as a reference to determine if the amount of detectable label is altered (decreased or increased). The predetermined microorganism in its non-resistant form may be added to the sample, or may be presented in a separate preparation. The predetermined microorganism in its non-resistant form may carry at least one further label. Any label as described herein may be employed, provided it is suitable for discrimination from the label of the antibiotic or/and other micro-organisms present in the assay of the present invention. The amount of detectable label in a predetermined microorganism in its non-resistant form may also be provided in the form of specific values or ranges of the amount of detectable label for one or more combinations of the micro-organism, an antibiotic and a labelling group, for instance in the form of a data sheet. In particular, a kit of the present invention may comprise said predetermined micro-organism in its non-resistant form or/and said data sheet.

The method of the present invention may also employ the predetermined micro-organism in its resistant form as a further control, or specific values or ranges of the amount of detectable label in a predetermined microorganism in its resistant form for one or more combinations of the micro-organism, an antibiotic and a labelling group, for instance in the form of a data sheet. The predetermined microorganism in its resistant form may carry at least one further label. Any label as described herein may be employed, provided it is suitable for discrimination from the label of the antibiotic or/and other micro-organisms present in the assay of the present invention. In particular, a kit of the present invention may comprise said predetermined micro-organism in its resistant form or/and said data sheet.

The decrease of the amount of detectable label may be at least 5%, at least 10%, at least 20%, at least 30%, at least 40%, at least 50%, at least 60%, at least 70%, at least 80%, or at least 90% with respect to the amount of detectable label in the predetermined micro-organism in its non-resistant form. In particular, a micro-organism to be identified may be a micro-organism essentially not carrying the label.

The increase of the amount of detectable label may be at least 5%, at least 10%, at least 20%, at least 30%, at least 40%, at least 50%, at least 60%, at least 70%, at least 80%, at least 90%, at least 100%, at least 150%, or at least 200% with respect to the amount of detectable label in the predetermined micro-organism in its non-resistant form.

In yet another embodiment of the present invention, the method comprises identification of the micro-organism in the biological sample. "Identification" in the context of the present invention refers to identification of individual microbial cells as belonging to a particular taxonomic category, such as species, genus, family, class or/and order, etc. Identification can be performed based on morphological or/and biochemical classifications.

A probe may be employed for identifying the micro-organism. It is preferred to identify the predetermined micro-organism by a labelled nucleic acid, in particular a labelled oligonucleotide, capable of specifically hybridising with a nucleic acid in the micro-organism under in-situ conditions. The labelled oligonucleotide may have a length of up to 50 nucleotides. More preferred is identification of the micro-organism by fluorescence in-situ hybridisation (FISH). These preferred and more preferred embodiments allow the detection of the antibiotic phenotype at the molecular level while maintaining in-situ hybridisation conditions to allow the simultaneous and unambiguous identification via in-situ hybridisation and the detection of an antibiotic resistance phenotype within the same cell—even if in a mixed population.

An in-situ hybridisation protocol may be applied as laid down in patent application EP 06 021 267.7, which is incorporated herein by reference. The incubation with a labelled antibiotic may be performed at temperatures below the $T_m$ of the hybridised probe. In a preferred embodiment the temperature is between about 25 and about 65° C., in a more preferred embodiment the temperature is between about 35° C. and about 59° C. In an even more preferred embodiment, the temperature is at about 52° C. The incubation time is preferably between about 1 and about 30 minutes. In a more preferred embodiment the incubation is made for about 15 minutes. After the incubation the slide may be submerged in 50% ethanol followed by a bath in pure ethanol. Both steps may be run for between about 1 and about 10 minutes. The preferred length of incubation is between about 2 and about 6 minutes. It is more preferred to incubate about 4 minutes. The slides may then be air-dried (e.g. on a hot plate) and the cells may be embedded in a balanced salt mounting medium.

The microorganism may be detected by any suitable method known in the art. The reading of the assay may require a resolution down to the individual cell. In particular, the micro-organism is detected via epifluorescence microscopy, flow cytometry, laser scanning devices, time resolved fluorometry, luminescence detection, isotope detection, hyper spectral imaging scanner, Surface Plasmon Resonance or/and another evanscesence based reading technology.

Preferably, in-situ hybridisation is combined with detection of antibiotic resistance. More preferably, FISH is combined with detection of antibiotic resistance.

It is also preferred that the predetermined micro-organism is identified in step (c) of the method of the present invention.

It is preferred that the identification of the micro-organism and the detection of the labelled antibiotic in the micro-organism are run subsequently.

In an alternative preferred embodiment, the identification of the micro-organism and the detection of the labelled antibiotic in the micro-organism are run concurrently. In this embodiment, the labelled antibiotic may be added to the hybridisation buffer. After the incubation the further treatment is performed as disclosed herein for the detection of the micro-organism. Most preferably, in-situ hybridisation and FISH, respectively, and detection of the antibiotic resistance are performed simultaneously.

Preferably, the same detection method, such as epifluorescence microscopy, flow cytometry, laser scanning devices or another method described herein, may be employed for both the identification of the micro-organism and the detection of the labelled antibiotic in the micro-organism.

In-situ hybridisation and enzyme or receptor assays conventionally call for specific environments for their respective assays of the state of the art. It was therefore surprising that it was possible to
1. prepare the cells for in-situ hybridisation with pores of sufficient size to allow passage of up to 50-mer oligo-nucleotides
2. make membrane proteins accessible for labelled antibiotics
3. maintain the integrity of both said proteins and ribosomes to allow the specific binding of antibiotics labelled with fluorophores
4. Find sufficient binding sites to generate a signal visible under an epifluorescence microscope, in particular under uniform conditions.

It is preferred to use in the method of the present invention an oligo-nucleotide with a fluorophor emitting at a predetermined wavelengths range together with an antibiotic labelled with another fluorophor emitting at a wavelengths range, so that the two fluorophors can be discriminated by luminescence detection. For instance, one of the fluorphors, such as Fluorescein, may emit a green signal, and the other fluorphor may emit a red signal. A list of antibiotics modified with a fluorophor is compiled in Table I.

In a most preferred embodiment, the method of the present invention comprises identification of a Methicillin Resistant *Staphylococcus aureus* (MRSA) by in-situ hybridisation simultaneously with the detection of the expression of the Penicillin Binding Protein 2 by binding a labelled β-Lactam antibiotic.

In the case of MRSA it is even possible to differentiate between nosocomial and community acquired MRSA by analysing the sensitivity towards Clindamycin or to Trimethoprim sulfa. Community acquired Methicillin resistant *Staphylococcus aureus* strains maintain their sensitivity towards Clindamycin or to Trimethoprim sulfa. The differentiation is then via the respective binding capacity profiles. In yet another most preferred embodiment, the method of the present invention thus comprises identification of a Methicillin Resistant *Staphylococcus aureus* (MRSA) by in-situ hybridisation simultaneously with the differentiation between nosocomial and community acquired MRSA via the respective ability to bind labelled Clindamycin or Trimethoprim sulfa.

In yet another most preferred embodiment, the method of the present invention comprises identification of a Vancomycin Resistant *Staphylococcus aureus* (VRSA) by in-situ hybridisation simultaneously with the ability to bind labelled Vancomycin.

In yet another most preferred embodiment, the method of the present invention comprises identification of a Vancomycin Resistant *Staphylococcus* (VRS) by in-situ hybridisation simultaneously with the ability to bind labelled Vancomycin.

In yet another most preferred embodiment, the method of the present invention comprises identification of a Vancomycin Resistant Enterococci (VRE) by in-situ hybridisation simultaneously with the ability to bind labelled Vancomycin.

In yet another most preferred embodiment, the method of the present invention comprises detection of a resistance towards β-lactam antibiotics due to the secretion of β-lactamases (ESBL) by the revealing of the presence of said enzyme by the binding of labelled clavulanic acid together with the identification of Gram negative micro-organisms.

Clavulanic acid is a beta-lactamase inhibitor sometimes combined with penicillin group antibiotics to overcome certain types of antibiotic resistance. Specifically, it is used to overcome resistance in bacteria that secrete beta-lactamase enzymes, which otherwise inactivate most penicillins. Most commonly, the potassium salt potassium clavulanate is combined with amoxicillin. Clavulanic acid is a competitive inhibitor of beta-lactam antibiotics. When labelled with a fluorophor it will detect the of presence beta-lactamases.

In yet another most preferred embodiment, the method of the present invention comprises detection of a resistance towards 1'-lactam antibiotics due to the secretion of metalo-β-lactamases (MBL) by the revealing of the presence of said enzyme by the binding of labelled imipenem together with the identification of Gram negative micro-organisms.

In yet another most preferred embodiment, the method of the present invention comprises detection of a resistance to macrolides, lincosamide and streptogramin (MLS) via the binding of labelled erythromycin or/and Clindamycin together with the identification of Streptococci.

In yet another most preferred embodiment, the method of the present invention comprises identification of a drug resistant *Streptococcus pneumoniae* (DRSP) with FISH together with the respective resistance towards beta-lactams and macrolides.

In yet another most preferred embodiment, the method of the present invention comprises detection of high level Aminoglycoside resistant Enterococci (HLAR) via FISH and labelled Gentamycin.

The biological sample comprising the predetermined micro-organisms may be pretreated in order to facilitate binding of the labelled antibiotic and optionally identification of the micro-organism.

The biological sample may be heat-fixed on a slide according to their designated probes (labelled antibiotic and optionally a probe for detecting the micro-organism), for instance at about 45 to about 65° C., preferably at about 50 to about 55° C., more preferably at about 52° C.

If the micro-organism is a Gram positive bacterium, it may be perforated by a suitable buffer. Gram positive cells may be perforated with a bacteriocin or/and a detergent. In a preferred embodiment a lantibiotic is combined with a biological detergent, and a specially preferred embodiment NISIN is combined with Saponin. In addition lytic enzymes such as Lysozyme and Lysostaphin may be applied. Lytic enzymes may be balanced into the equation. If the sample is treated with ethanol, the concentration of the active ingredients may be balanced with respect to their subsequent treatment in ethanol. In a more preferred embodiment the concentration of Lysozyme, Lysostaphin, Nisin and Saponin is balanced to cover all Gram positive organisms with the exception of Mycobacteria.

An example of a most preferred Gram Positive Perforation Buffer is given in Table 2. It is contemplated that variations of the amounts and concentrations, and application temperatures and incubation times are within the skill in the art.

If the micro-organism is a yeast or a mould, it may be perforated by a suitable buffer. Surprisingly it was found that the cell walls of yeasts and moulds did not form reproducible pores when treated following procedures well known in the art. These procedures frequently rendered both false positive and false negative results. A reliable solution is a preferred buffer comprising a combination of a peptide antibiotic, detergent, complexing agent, and reducing agent. A more preferred buffer comprises the combination of a mono-valent salt generating a specific osmotic pressure, a bacteriocin, a combination of biological and synthetic detergents, a complexing agent for divalent cations, and an agent capable of reducing disulfide bridges. A further surprising improvement was achieved by adding proteolytic enzymes specific for prokaryotes. In an even more preferred buffer, Saponin, SDS, Nisin, EDTA, DTT were combined with Lysozyme and a salt, for in stance in a concentration of about 150 to about 250 mM, more preferably about 200 to about 230 mM, most preferably about 215 mM.

An example of a most preferred Yeast Perforation Buffer is given in Table 2. It is contemplated that variations of the amounts and concentrations, and application temperatures and incubation are within the skill in the art.

In yet another preferred embodiment, the method of the present invention is a diagnostic method.

Yet another aspect of the present invention is a kit suitable for detecting an antibiotic resistance in a predetermined micro-organism, comprising
(a) a labelled antibiotic, and
(b) optionally a probe suitable for identification of the micro-organism in the biological sample.

The kit of the present invention is suitable in the method of the present invention. The labelled antibiotic may be a labelled antibiotic as described herein in the context of the method of the present invention.

The probe may be any probe suitable for identification of a microorganism. It is preferred that the probe is a labelled nucleic acid, in particular a labelled oligonucleotide, capable of specifically hybridising with a nucleic acid in the micro-organism under in-situ conditions. The oligonucleotide may have a length up to 50 nucleotides.

As indicated above, the kit may comprise further components, such as a data sheet providing information about the amount of detectable label in at least one combination of micro-organism, antibiotic and label, or a sample of a predetermined micro-organism in its non-resistant or/and resistant form, e.g. for control purposes.

Yet another aspect of the present invention is the use of a labelled antibiotic for the detection of an antibiotic resistance in a predetermined micro-organism in a biological sample.

The present invention is further illustrated by the following examples and the following tables.

Table 1 describes the antibiotics and examples of labelling suitable in the method of the present invention.

Table 2 describes the composition of perforation buffers employed in the present invention.

Table 3: Antibiotic resistance due to mutations on the 23S rRNA.

Table 4: Antibiotic resistance mechanism in micro-organisms and alteration in the amount of labelled antibiotics in resistant micro-organisms.

EXAMPLE 1

The antibiotics of Table I were labelled with FITC and purified as is well known in the art. Clindamycin was modified by substituting the methyl group attached to the X'—S with cysteine via an S—S bond. The attached cysteine was then labelled with Fluorescamin either via an N-hydroxy-succinimide ester or FITC and purified with methods well known in the art.

EXAMPLE 2

An antibiotic resistance, such as a resistance against penicillin, may be detected in a protocol comprising the steps:

| | |
|---|---|
| 1 | Apply the biological sample to slide, e.g. 10 μl |
| 2 | Dry, for instance at 52° C. |
| 3 | Add perforation buffer, e.g. 10 μl |
| 4 | Dry |
| 5 | Add reconstituted probe mix (e.g. 9 μl) |
| 6 | Add antibiotic (e.g. FITC-penicillin) |
| 7 | Incubate, e.g. for 15 min at 52° C. |
| 8 | EtOH/Stop mix (e.g. 50%:50%), e.g. for 5 min at RT |
| 9 | Ethanol, e.g. 99% ethanol for 5 min |
| 10 | Dry |
| 11 | Balanced Salt Mounting Medium (e.g. one small drop) |
| 12 | Read |

EXAMPLE 3

Table 4 indicates the alteration of the amount of detectable labelled antibiotics in clinically relevant micro-organisms in its resistant form relative to its non-resistant form. The amount is expressed in % change of fluorescence (decrease and increase, respectively) of an antibiotic which carries a fluorescent label.

TABLE 1

| Antibiotics | | |
|---|---|---|
| Generic Name | Examples of Labelling agent | |
| Aminoglycosides | | |
| Amikacin | FITC | Atto-495-NSI |
| Gentamicin | FITC | Atto-495-NSI |
| Kanamycin | FITC | Atto-495-NSI |
| Neomycin | FITC | Atto-495-NSI |
| Netilmicin | FITC | Atto-495-NSI |
| Streptomycin | FITC | Atto-495-NSI |
| Tobramycin | FITC | Atto-495-NSI |
| | FITC | Atto-495-NSI |
| Carbacephem | | |
| Loracarbef | FITC | Atto-495-NSI |

TABLE 1-continued

Antibiotics

| Generic Name | Examples of Labelling agent | |
|---|---|---|
| Carbapenems | | |
| Ertapenem | FITC | Atto-495-NSI |
| Imipenem | FITC | Atto-495-NSI |
| Cilastatin | FITC | Atto-495-NSI |
| Meropenem | FITC | Atto-495-NSI |
| Cephalosporins First generation | | |
| Cefadroxil | FITC | Atto-495-NSI |
| Cefazolin | FITC | Atto-495-NSI |
| Cephalexin | FITC | Atto-495-NSI |
| Cephalosporins Second generation | | |
| Cefaclor | FITC | Atto-495-NSI |
| Cefamandole | FITC | Atto-495-NSI |
| Cefoxitin | FITC | Atto-495-NSI |
| Cefprozil | FITC | Atto-495-NSI |
| Cefuroxime | FITC | Atto-495-NSI |
| Cephalosporins Third generation | | |
| Cefixime | FITC | Atto-495-NSI |
| Cefdinir | FITC | Atto-495-NSI |
| Cefditoren | FITC | Atto-495-NSI |
| Cefoperazone | FITC | Atto-495-NSI |
| Cefotaxime | FITC | Atto-495-NSI |
| Cefpodoxime | FITC | Atto-495-NSI |
| Ceftazidime | FITC | Atto-495-NSI |
| Ceftibuten | FITC | Atto-495-NSI |
| Ceftizoxime | FITC | Atto-495-NSI |
| Ceftriaxone | FITC | Atto-495-NSI |
| Cefsulodine | FITC | Atto-495-NSI |
| Cephalosporins Fourth generation | | |
| Cefepime | FITC | Atto-495-NSI |
| Glycopeptides | | |
| Teicoplanin | FITC | Atto-495-NSI |
| Vancomycin | FITC | Atto-495-NSI |
| Macrolides | | |
| Azithromycin | Coupling of FITC with Erythro mycylamine | Coupling of Erythro mycylamine with Atto-495-NSI |
| Clarithromycin | | |
| Dirithromycin | | |
| Erythromycin | | |
| Roxithromycin | | |
| Troleandomycin | | |
| Monobactam | | |
| Aztreonam | FITC | Atto-495-NSI |
| Penicillins | | |
| Amoxicillin | FITC | Atto-495-NSI |
| Ampicillin | FITC | Atto-495-NSI |
| Azlocillin | | |
| Carbenicillin | | |
| Cloxacillin | | |
| Dicloxacillin | | |
| Flucloxacillin | | |
| Mezlocillin | | |
| Nafcillin | | |
| Penicillin | | |
| Piperacillin | | |
| Ticarcillin | | |
| Polypeptides | | |
| Bacitracin | FITC | Atto-495-NSI |
| Colistin | FITC | Atto-495-NSI |
| Polymyxin B | FITC | Atto-495-NSI |
| Quinolones | | |
| Ciprofloxacin | | |
| Enoxacin | | |
| Gatifloxacin | | |
| Levofloxacin | | |
| Lomefloxacin | | |
| Moxifloxacin | | |
| Norfloxacin | | |
| Ofloxacin | | |
| Trovafloxacin | | |
| Sulfonamides | | |
| Mafenide | FITC | Atto-495-NSI |
| Prontosil (archaic) | FITC | Atto-495-NSI |
| Sulfacetamide | FITC | Atto-495-NSI |
| Sulfamethizole | FITC | Atto-495-NSI |
| Sulfanilimide (archaic) | FITC | Atto-495-NSI |
| Sulfasalazine | FITC | Atto-495-NSI |
| Sulfisoxazole | FITC | Atto-495-NSI |
| Trimethoprim sulfa | FITC | Atto-495-NSI |
| Trimethoprim | FITC | Atto-495-NSI |
| Sulfamethoxazole | FITC | Atto-495-NSI |
| Co-trimoxazole | FITC | Atto-495-NSI |
| TMP-SMX | FITC | Atto-495-NSI |
| Tetracyclines | | |
| Demeclocycline | FITC | Atto-495-NSI |
| Doxycycline | FITC | Atto-495-NSI |
| Minocycline | FITC | Atto-495-NSI |
| Oxytetracycline | FITC | Atto-495-NSI |
| Tetracycline | FITC | Atto-495-NSI |
| Others | | |
| Chloramphenicol | | |
| Clindamycin | Cysteine + FITC | Cystein + Atto-495-NSI |
| Ethambutol | | |
| Fosfomycin | | |
| Furazolidone | | |
| Isoniazid | | |
| Linezolid | | |
| Metronidazole | | |
| Mupirocin | | |
| Nitrofurantoin | | |
| Platensimycin | | |
| Pyrazinamide | | |
| Quinupristin/ Dalfopristin | | |
| Rifampin | | |
| Spectinomycin | | |
| Amphotericin B | FITC | Atto-495-NSI |
| Flucanazole | | |
| Fluoropyrimidins | | |

TABLE 2

Gram-Positive Perforation Buffer-

| 50 µg/ml | Saponin |
|---|---|
| 5 µg/ml | Nisin |
| 20 mM | Tris pH 8 |
| 100 µg/m | Lysozym |
| 50 µg/ml | Lysostaphin |
| | H$_2$O |

Working soln.
Yeast Perforation Buffer

| 500 µg/ml | Saponin |
|---|---|
| 10 µg/ml | Nisin |
| 50 mM | Tris pH 8.3 |
| 215 mM | NaCl |
| 0.1% | SDS |
| 5 mM | EDTA |
| 10 mM | DTT |
| 100 µg/ml | Lysozyme |
| | H$_2$O |

TABLE 3

Compilation of antibiotic resistance due to mutations on the 23S rRNA

| Type of RNA | Position | Alteration(s) | Phenotype | Organism | Reference |
|---|---|---|---|---|---|
| 23S | 2032 | AG to GA | Clr/Azm/Ery-R | *Helicobacter pylori* | Húlten, K., A. Gibreel, O. Sköld, and L. Engstrand. 1997. Macrolide resistance in *Helicobacter pylori*: mechanism and stability in strains from clarithromycin-treated patients. Antimicrob. Agents Chemother. 41: 2550-2553. |
| 23S | 2058 | A to C | Clr-R | *Helicobacter pylori* | Stone, G. G., D. Shortridge, R. K. Flamm, J. Versalovic, J. Beyer, K. Idler, L. Zulawinski, and S. K. Tanaka. 1996. Identification of a 23S rRNA gene mutation in clarithromycin-resistant *Helicobacter pylori*. *Helicobacter*. 1: 227-228. |
| 23S | 2058 | A to C | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2058 | A to C | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to C | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2058 | A to G | Cla-R | *Helicobacter pylori* | Versalovic, J., D. Shortridge, K. Kibler, M. V. Griffy, J. Beyer, R. K. Flamm, S. K. Tanaka. D. Y. Graham, and M. F. Go. 1996. Mutations in 23S rRNA are associated with clarithromycin resistance in *Helicobacter pylori*. Antimicrob. Agents Chemother. 40: 4 |
| 23S | 2058 | A to G | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2058 | A to G | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to G | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2058 | A to U | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to U | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2059 | A to C | Mac-R, Lin-R, SB-S | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2059 | A to C | Clr-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2059 | A to G | Clr-R | *Helicobacter pylori* | Versalovic, J., D. Shortridge, K. Kibler, M. V. Griffy, J. Beyer, R. K. Flamm, S. K. Tanaka. D. Y. Graham, and M. F. Go. 1996. Mutations in 23S rRNA are associated with clarithromycin resistance in |

TABLE 3-continued

Compilation of antibiotic resistance due to mutations on the 23S rRNA

| Type of RNA | Position | Alteration(s) | Phenotype | Organism | Reference |
|---|---|---|---|---|---|
| | | | | | *Helicobacter pylori*. Antimicrob. Agents Chemother. 40:4 |
| 23S | 2059 | A to G | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2059 | A to G | Mac-R, Lin-R, SB-S | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2059 | A to G | Cla-R | *Helicobacter pylori* | Debets-Ossenkopp. Y. J., A. B. Brinkman E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 754 | "U to A" | Resistant to low concentrations of ketolide HMR3647; resistant to erythromycin b. | *E. coli* | Xiong L, Shah S, Mauvais P, Mankin A S. 1999. A ketolide resistance mutation in domain II of 23S rRNA reveals the proximity of hairpin 35 to the peptidyl transferase center. Molecular Microbiology 31 (2): 633-639. |
| 23S | 754 | "U to A" | Confers macrolide and ketolide resistance. | *E. coli* | Hansen L. H., Mauvais P, Douthwaite S. 1999. The macrolide-ketolide antibiotic binding site is formed by structures in domain II and V of 23S ribosomal RNA. Molecular Microbiology 31 (2): 623-631. |
| 23S | 754 | U to A | Ery-LR, Tel-LR | *Escherichia coli* | Xiong, L., S. Shah, P. Mauvais, and A. S. Mankin. 1999. A ketolide resistance mutation in domain II of 23S rRNA reveals the proximity of hairpin 35 to the peptidyl transferase centre. Mol. Microbiol. 31: 633-639. |
| 23S | 1005 | C to G | Slow growth under natural promoter; (with 2058G and erythromycin) severe growth retardation. A | *E. coli* | 1) Rosendahl, G. and Douthwaite, S. (1995) Nucleic Acids Res. 23, 2396-2403. 2) Rosendahl, G., Hansen, L. H., and Douthwaite, S. (1995) J. Mol. Biol. 249, 59-68. |
| 23S | 1005 | C to G | Slow growth under pL promoter; (with 2058G and erythromycin) Erys. a Double mutant (C1005G/C1006U) | *E. coli* | 1) Rosendahl, G. and Douthwaite, S. (1995) Nucleic Acids Res. 23, 2396-2403. 2) Rosendahl, G., Hansen, L. H., and Douthwaite, S. (1995) J. Mol. Biol. 249, 59-68. |
| 23S | 1006 | C to U | Slow growth under pL promoter; (with 2058G and erythromycin) Erys. a Double mutant (C1005G/C1006U) | *E. coli* | 1) Rosendahl, G. and Douthwaite, S. (1995) Nucleic Acids Res. 23, 2396-2403. 2) Rosendahl, G., Hansen, L. H., and Douthwaite, S. (1995) J. Mol. Biol. 249, 59-68. |
| 23S | 1006 | C to U | Lethal under natural promoter; under pL promoter; (with 2058G and erythormycin) Erys. A | *E. coli* | 1) Rosendahl, G. and Douthwaite, S. (1995) Nucleic Acids Res. 23, 2396-2403. 2) Rosendahl, G., Hansen, L. H., and Douthwaite, S. (1995) J. Mol. Biol. 249, 59-68. |
| 23S | 1056 | G to A | Binding of both L11 and thiostrepton is weakened in RNA fragments. B | *E. coli* | Ryan, P. C. and Draper, D. E. (1991) Proc. Natl. Acad. Sci. USA 88, 6308-6312. |
| 23S | 1056 | G to A | Stoichiometric L11 binding.b (with 2058G and erythromycin) Reduced growth rate. a | *E. coli* | 1) Douthwaite, S. and Aagaard, C. (1993) J. Mol. Biol. 232, 725-731. 2) Rosendahl, G. and Douthwaite, S. (1995) Nucleic Acids Res. 23, 2396-2403. |
| 23S | 1056 | G to C | Binding of thiostrepton is weakened in RNA fragments. B | *E. coli* | Ryan, P. C. and Draper, D. E. (1991) Proc. Natl. Acad. Sci. USA 88, 6308-6312. |
| 23S | 1064 | C to U | Stoichiometric L11 binding. b (with 2058G and erythromycin) Reduced growth rate. a | *E. coli* | 1) Douthwaite, S. and Aagaard, C. (1993) J. Mol. Biol. 232, 725-731. 2) Rosendahl, G. and Douthwaite, S. (1995) Nucleic Acids Res. 23, 2396-2403. |
| 23S | 1067 | A to U | Normal growth | *E. coli* | 1) Spahn, C., Remme, J., Schafer, M. and Nierhaus, K. (1996). J. Biol. Chem. 271: 32849-32856. 2) Spahn, C., Remme, J., Schafer, M. and Nierhaus, K. (1996). J. Biol. Chem. 271: 32857-32862. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 1067 | A to G | Thiostrepton resistance in *Halobacterium* sp. | *Halobacterium* | Hummel, H., and A. Böck. (1987) Biochimie 69: 857-861. |
| 23S | 1067 | A to U | Thiostrepton resistance in *Halobacterium* sp. | *Halobacterium* | Hummel, H., and A. Böck. (1987) Biochimie 69: 857-861. |
| 23S | 1067 | A to U | A to C or U confers high level resistance to thiostrepton, whereas A to G confers intermediate level resistance; drug binding affinity is reduced similarly. a, b Expression by host RNA polymerase results in formation of active ribosomal subunits in vivo. A | *E. coli* | 1) Thompson, J. and Cundliffe, E. (1991) Biochimie 73: 1131-1135. 2) Thompson, J., Cundliffe, E. and Dahlberg, A. E. (1988) J. Mol. Biol. 203: 457-465. 3) Lewicki, B. T. U., Margus, T., Remme, J. and Nierhaus, K. H. (1993) J. Mol. Biol. 231, 581-593. 4) LAST |
| 23S | 1067 | A to C | A to C or U confers high level resistance to thiostrepton, whereas A to G confers intermediate level resistance; drug binding affinity is reduced similarly. a, b Expression by host RNA polymerase results in formation of active ribosomal subunits in vivo. A | *E. coli* | 1) Thompson, J. and Cundliffe, E. (1991) Biochimie 73: 1131-1135. 2) Thompson, J., Cundliffe, E. and Dahlberg, A. E. (1988) J. Mol. Biol. 203: 457-465. 3) Lewicki, B. T. U., Margus, T., Remme, J. and Nierhaus, K. H. (1993) J. Mol. Biol. 231, 581-593. 4) LAST |
| 23S | 1067 | A to G | A to C or U confers high level resistance to thiostrepton, whereas A to G confers intermediate level resistance; drug binding affinity is reduced similarly. a, b Expression by host RNA polymerase results in formation of active ribosomal subunits in vivo. A | *E. coli* | 1) Thompson, J. and Cundliffe, E. (1991) Biochimie 73: 1131-1135. 2) Thompson, J., Cundliffe, E. and Dahlberg, A. E. (1988) J. Mol. Biol. 203: 457-465. 3) Lewicki, B. T. U., Margus, T., Remme, J. and Nierhaus, K. H. (1993) J. Mol. Biol. 231, 581-593. 4) LAST |
| 23S | 1067 | "A to U" | Constituted 30% of the total 23S rRNA pool in the ribosomes; exhibited 30% thiostrepton resistance in poly (U) translation b. | *E. coli* | Liiv A, Remme J. 1998. Base-pairing of 23S rRNA ends is essential for ribosomal large subunit assembly. J. Mol. Biol. 285: 965-975. |
| 23S | 1068 | G to A | Reduced L11 binding. b (with 2058G) Lethal when expressed from rrnB or pL promotor in presence of erythromycin. A | *E. coli* | 1) Rosendahl, G. and Douthwaite, S. (1995) Nucleic Acids Res. 23, 2396-2403. 2) Douthwaite, S. and Aagaard, C. (1993) J. Mol. Biol. 232, 725-731. |
| 23S | 1068 | G to A | Suppression of 1068A; lethality only in absence of erythromycin. a Double mutant (G1068A/G1099A) | *E. coli* | Rosendahl, G. and Douthwaite, S. (1995) Nucleic Acids Res. 23, 2396-2403. |
| 23S | 1072 | C to U | Lethal when expressed from rrnB or pL promotor in presence of erythromycin. a | *E. coli* | Rosendahl, G. and Douthwaite, S. (1995) Nucleic Acids Res. 23, 2396-2403. |
| 23S | 1137 | G to A | With 2058G and erythromycin, lethal when expressed from rrnB promoter. | *E. coli* | Rosendahl, G., Hansen, L. H., and Douthwaite, S. (1995) J. Mol. Biol. 249, 59-68. |
| 23S | 1137 | G to A | Restores normal growth under pL promoter; (With 2058G and erythromycin) Eryr. Double mutant (G1137A/C1006U) | *E. coli* | Rosendahl, G., Hansen, L. H., and Douthwaite, S. (1995) J. Mol. Biol. 249, 59-68. |
| 23S | 1137 | G to A | With 2058G and erythromycin, lethal when expressed from rrnB promoter. Double mutant (G1137A/G1138C) | *E. coli* | Rosendahl, G., Hansen, L. H., and Douthwaite, S. (1995) J. Mol. Biol. 249, 59-68. |
| 23S | 1138 | G to C | With 2058G and erythromycin, lethal when expressed from rrnB promoter. | *E. coli* | Rosendahl, G., Hansen, L. H., and Douthwaite, S. (1995) J. Mol. Biol. 249, 59-68. |
| 23S | 1138 | G to C | With 2058G and erythromycin, lethal when expressed from rrnB promoter. Double mutant (G1138C/G1137A) | *E. coli* | Rosendahl, G., Hansen, L. H., and Douthwaite, S. (1995) J. Mol. Biol. 249, 59-68. |
| 23S | 1207 | C to U | Erythromycin resistant. a Double mutant (C1207U/C1243U) | *E. coli* | Dam, M., Douthwaite, S., Tenson, T. and Mankin, A. S. (1996) J. Mol. Biol. 259, 1-6. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 1208 | C to U | Erythromycin resistant. a Double mutant (C1208U/C1243U) | E. coli | Dam, M., Douthwaite, S., Tenson, T. and Mankin, A. S. (1996) J. Mol. Biol. 259, 1-6. |
| 23S | 1211 | C to U | Erythromycin sensitive. a Double mutant (C1211U/C1208U) | E. coli | Dam, M., Douthwaite, S., Tenson, T. and Mankin, A. S. (1996) J. Mol. Biol. 259, 1-6. |
| 23S | 1220 | G to A | Erythromycin resistant. a Double mutant (G1220A/G1239A) | E. coli | Dam, M., Douthwaite, S., Tenson, T. and Mankin, A. S. (1996) J. Mol. Biol. 259, 1-6. |
| 23S | 1221 | C to U | Erythromycin resistant. a Double mutant (C1221U/C1229U) | E. coli | Dam, M., Douthwaite, S., Tenson, T. and Mankin, A. S. (1996) J. Mol. Biol. 259, 1-6. |
| 23S | 1221 | C to U | Erythromycin resistant. a Double mutant (C1221U/C1233U) | E. coli | Dam, M., Douthwaite, S., Tenson, T. and Mankin, A. S. (1996) J. Mol. Biol. 259, 1-6. |
| 23S | 1230 | 1230 | Erythromycin sensitive. a Double deletion (1230/1231) | E. coli | Douthwaite, S., Powers, T., Lee, J. Y., and Noller, H. F. (1989) J. Mol. Biol. 209, 655-665. |
| 23S | 1231 | 1231 | Erythromycin sensitive. a Double deletion (1231/1230) | E. coli | Douthwaite, S., Powers, T., Lee, J. Y., and Noller, H. F. (1989) J. Mol. Biol. 209, 655-665. |
| 23S | 1232 | G to A | Erythromycin sensitive. a Double mutant (G1232A/G1238A) | E. coli | Dam, M., Douthwaite, S., Tenson, T. and Mankin, A. S. (1996) J. Mol. Biol. 259, 1-6. |
| 23S | 1233 | C to U | Erythromycin sensitive. a | E. coli | Dam, M., Douthwaite, S., Tenson, T. and Mankin, A. S. (1996) J. Mol. Biol. 259, 1-6. |
| 23S | 1234 | "del1234/del1235" | Erythromycin sensitive. a Double mutant (U1234C/del1235) | E. coli | Douthwaite, S., Powers, T., Lee, J. Y., and Noller, H. F. (1989) J. Mol. Biol. 209, 655-665. |
| 23S | 1234 | U to C | Erythromycin sensitive. a | E. coli | Douthwaite, S., Powers, T., Lee, J. Y., and Noller, H. F. (1989) J. Mol. Biol. 209, 655-665. |
| 23S | 1243 | C to U | Erythromycin resistant. a Double mutant (C1243U/C1208U) | E. coli | Douthwaite, S., Powers, T., Lee, J. Y., and Noller, H. F. (1989) J. Mol. Biol. 209, 655-665. |
| 23S | 1243 | C to U | Erythromycin resistant. a Double mutant (C1243U/C1221U) | E. coli | Douthwaite, S., Powers, T., Lee, J. Y., and Noller, H. F. (1989) J. Mol. Biol. 209, 655-665. |
| 23S | 1243 | "C to U" | Erythromycin resistant. a Double mutant (C1243U/C1207). | E. coli | Douthwaite, S., Powers, T., Lee, J. Y., and Noller, H. F. (1989) J. Mol. Biol. 209, 655-665. |
| 23S | 1262 | A to G | With erythromycin; lethal | E. coli | Aagaard, C., and Douthwaite, S. (1994) Proc. Natl. Acad. Sci. USA 91, 2989-2993. |
| 23S | 1262 | A to C | With erythromycin; lethal | E. coli | Aagaard, C., and Douthwaite, S. (1994) Proc. Natl. Acad. Sci. USA 91, 2989-2993. |
| 23S | 1262 | A to U | With erythromycin; reduced growth rate | E. coli | Aagaard, C., and Douthwaite, S. (1994) Proc. Natl. Acad. Sci. USA 91, 2989-2993. |
| 23S | 1262 | A to C | With erythromycin; reduced growth rate Double mutant (A1262C/U2017G) | E. coli | Aagaard, C., and Douthwaite, S. (1994) Proc. Natl. Acad. Sci. USA 91, 2989-2993. |
| 23S | 1262 | A to G | Suppression of growth effects; Wild-type growth on erythromycin Double mutant (A1262G/U2017C) | E. coli | Aagaard, C., and Douthwaite, S. (1994) Proc. Natl. Acad. Sci. USA 91, 2989-2993. |
| 23S | 1262 | A to U | Suppression of growth effects; Wild-type growth on erythromycin Double mutant (A1262U/U2017A) | E. coli | Aagaard, C., and Douthwaite, S. (1994) Proc. Natl. Acad. Sci. USA 91, 2989-2993. |
| 23S | 1262 | A to U | With erythromycin; reduced growth rate Double mutant (A1262U/U2017G) | E. coli | Aagaard, C., and Douthwaite, S. (1994) Proc. Natl. Acad. Sci. USA 91, 2989-2993. |
| 23S | 1423 | G to A | Suppressed requirement for 4.5S RNA in translation of natural mRNAs by cell extracts. c | E. coli | O'Connor, M., Brunelli, C. A., Firpo, M. A., Gregory, S. T., Lieberman, K. R., Lodmell, J. S., Moine, H., Van Ryk, D. I. and Dahlberg, A. E. (1995) Biochem. Cell Biology 73, 859-868. |
| 23S | 1698 | A to G | Suppresses 2555 mutations | E. coli | O'Connor & Dahlberg, unpublished |
| 23S | 2017 | "U to G" | Reduced growth rate on eyrthomycin. | E. coli | Aaagard, C. and Douthwaite, S. (1994) Proc. Natl. Acad. Sci. USA 91, 2989-2993. |
| 23S | 2017 | "U to C" | Reduced growth rate of erythromycin. | E. coli | Aaagard, C. and Douthwaite, S. (1994) Proc. Natl. Acad. Sci. USA 91, 2989-2993. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2017 | "U to A" | Reduced growth rate of erythromycin. | E. coli | Aaagard, C. and Douthwaite, S. (1994) Proc. Natl. Acad. Sci. USA 91, 2989-2993. |
| 23S | 2017 | "U to C" | Reduced growth rate on erythromycin. Double mutation (U2017C/A1262G) | E. coli | Aaagard, C. and Douthwaite, S. (1994) Proc. Natl. Acad. Sci. USA 91, 2989-2993. |
| 23S | 2017 | "U to G" | Reduced growth rate on erythromycin. Double mutation (U2017G/A1262C) | E. coli | Aaagard, C. and Douthwaite, S. (1994) Proc. Natl. Acad. Sci. USA 91, 2989-2993. |
| 23S | 2017 | "U to G" | Reduced growth rate on erythromycin. Double mutation (U2017G/A1262U) | E. coli | Aaagard, C. and Douthwaite, S. (1994) Proc. Natl. Acad. Sci. USA 91, 2989-2993. |
| 23S | 2032 | "G to A" | Lincomycin resistance. | Tobbaco chloroplasts | Cseplö, A., Etzold, T., Schell, J., and Schreier, P. H. (1988) Mol. Genet. 214, 295-299. |
| 23S | 2032 | "G to A" | EryS, Cds, Cms. Double mutation (G2032A/A2058G) | E. coli | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2032 | "G to A" | Eryhs, Cds, Cms. Double mutation (G2032A/A2058U) | E. coli | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2032 | "G to A" | Eryr, Cdr, Cmr. Double mutation (G2032A/G2057A) | E. coli | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2032 | AG to GA | Clr/Azm/Ery-R | Helicobacter pylori | Húlten, K., A. Gibreel, O. Sköld, and L. Engstrand. 1997. Macrolide resistance in Helicobacter pylori: mechanism and stability in strains from clarithromycin-treated patients. Antimicrob. Agents Chemother. 41: 2550-2553. |
| 23S | 2051 | "del A" | Prevents ErmE methylation. c | E. coli | Vester B, Nielsen A K, Hansen L H, Douthwaite S. 1998. ErmE Methyltransferase Recognition Elements in RNA Substrates. J. Mol. Biol. 282: 255-264. |
| 23S | 2052 | "A to C" | Prevents ErmE methylation. c | E. coli | Vester B, Nielsen A K, Hansen L H, Douthwaite S. 1998. ErmE Methyltransferase Recognition Elements in RNA Substrates. J. Mol. Biol. 282: 255-264. |
| 23S | 2052 | "A to G" | Like A2052C. c | E. coli | Vester B, Nielsen A K, Hansen L H, Douthwaite S. 1998. ErmE Methyltransferase Recognition Elements in RNA Substrates. J. Mol. Biol. 282: 255-264. |
| 23S | 2052 | "A to U" | Like A2052C. c | E. coli | Vester B, Nielsen A K, Hansen L H, Douthwaite S. 1998. ErmE Methyltransferase Recognition Elements in RNA Substrates. J. Mol. Biol. 282: 255-264. |
| 23S | 2057 | "G to A" | Eryr, Clinidamycin (Cd)s, Chloramphenicol (Cm)r; reduces methylation of 23S rRNA by ErmE. | E. coli | 1. Ettayebi, M., Prasad, S. M., and Morgan, E. A. (1985) J. Bacteriol. 162, 551-557 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2057 | "G to A" | Eyrr. | Chlamydomonas reinhardtii | Harris, E. H., Burkhart, B. D., Gilham, N. W., and Boynton, J. E. (1989) Genetics 123, 281-292. |
| 23S | 2057 | "G to A" | Slightly Eryr; reduced methylation. Double mutation (G2057A/C2661U) | E. coli | Vester, B., Hansen, L. H., and Douthwaite, S. (1995) RNA 1, 501-509. |
| 23S | 2057 | "G to A" | Eryr, Cdr, Cmr. Double mutation (G2057A/G2032A) | E. coli | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2057 | G to A | Ery-R, Lin-S | *Chlamydomonas reinhardtii* chl. | Harris, E. H., B. D. Burkhart, N. W. Gillham, and J. E. Boynton. 1989. Antibiotic resistance mutations in the chloroplast 16S and 23S rRNA genes of *Chlamydomonas reinhardtii*: correlation of genetic and physical maps of the chloroplast genome. Genetics. |
| 23S | 2057 | G to A | Ery-R, M16-S, Lin-S, SB-S | *Escherichia coli* | Ettayebi, M., S. M. Prasad, and E. A. Morgan. 1985. Chloramphenicol-erythromycin resistance mutations in a 23S rRNA gene of *Escherichia coli*. J. Bacteriol. 162: 551-557. |
| 23S | 2057 | G to A | Ery-LR, M16-S | *Propionibacteria* | Ross, J. I., E. A. Eady, J. H. Cove, C. E. Jones, A. H. Ratyal, Y. W. Miller, S. Vyakrnam, and W. J. Cunliffe. 1997. Clinical resistance to erythromycin and clindamycin in cutaneous propionibacteria isolated from acne patients is associated with mutatio |
| 23S | 2057 | GG to AA | Ery-R, Lin-R | *Escherichia coli* | Douthwaite, S. 1992. Functional interactions within 23S rRNA involving the peptidyltransferase center. J. Bacteriol. 174: 1333-1338. |
| 23S | 2058 | "A to G" | Eryr, Lincomycin and clindamycin resistance. | *Chlamydomonas reinhardtii* | Harris, E. H., Burkhart, B. D., Gilham, N. W., and Boynton, J. E. (1989) Genetics 123, 281-292. |
| 23S | 2058 | "A to G" | Clarithromycin resistance | *Helecobacter pylori* | Versalovic, J., Shortridge, D., Kibler, K., Griffy, M. V., Beyer, J., Flamm, R. K., Tenaka, S. K., Graham, D. Y., and Go, M. F. (1996) Antimicrob. Agents Chemother. 40, 477-480. |
| 23S | 2058 | "A to G" | Eryr, Cdr, Cms; abolishes methylation of 23S rRNA by ErmE. | *E. coli* | 1. Vester, B. and Garrett, R. A. (1988) EMBO J. 7, 3577-3587. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2058 | "A to G" | Erythromycin resistance. | Yeast mitochondria | Sor, F. and Fukuhara, H. (1982) Nucleic Acids Res. 10, 6571-6577. |
| 23S | 2058 | "A to G" | Lincomycin resistance. | *Solanum nigrum* | Kavanagh, T. A., O'Driscoll, K. M., McCabe, P. F., and Dix, P. J. (1994) Mol. Gen. Genet. 242, 675-680. |
| 23S | 2058 | "A to G" | Lincomycin resistance. | Tobacco chloroplasts | Cseplö, A., Etzold, T., Schell, J., and Schreier, P. H. (1988) Mol. Genet. 214, 295-299. |
| 23S | 2058 | "A to G" | EryS, Cds, Cms. Double mutation (A2058G/G2032A). | *E. coli* | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2058 | "A to U" | Eryhs, Cds, Cms. Double mutation (A2058U/G2032A). | *E. coli* | 1. Douthwaite, S. (1992) J. Bacteriol. 174, 1333-1338. 2. Aaagard, C. and Douthwaite, S. (1994) Proc. Natl. Acad. Sci. USA 91, 2989-2993. 3. Vester, B., Hansen, L. H., and Douthwaite, S. (1995) RNA 1, 501-509. |
| 23S | 2058 | "A to C" | Confers resistance to the MLS drugs and chloramphenicol. | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2058 | "A to G" | Like A2058C | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2058 | "A to U" | Like A2058C | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2058 | A to G/U | Ery-R, Tyl-R, Lin-R | *Brachyspira hyodysenteriae* | Karlsson, M., C. Fellstrom, M. U. Heldtander, K. E. Johansson, and A. Franklin. 1999. Genetic basis of macrolide and lincosamide resistance in *Brachyspira* |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2058 | A to G | Ery-R, Lin-R | *Chlamydomonas reinhardtii* chl. | (*Serpulina*) *hyodysenteriae*. FEMS Microbiol. Lett. 172: 255-260. Harris, E. H., B. D. Burkhart, N. W. Gillham, and J. E. Boynton. 1989. Antibiotic resistance mutations in the chloroplast 16S and 23S rRNA genes of *Chlamydomonas reinhardtii*: correlation of genetic and physical maps of the chloroplast genome. Genetics. |
| 23S | 2058 | A to G | Ery-R, Lin-R | *Escherichia coli* | Douthwaite, S. 1992. Functional interactions within 23S rRNA involving the peptidyltransferase center. J. Bacteriol. 174: 1333-1338. Vester, B., and R. A. Garrett. 1987. A plasmid-coded and site-directed mutation in *Escherichia coli* 23S RNA that confers |
| 23S | 2058 | A to U | MLSB-R | *Escherichia coli* | Sigmund, C. D., M. Ettayebi, and E. A. Morgan. 1984. Antibiotic resistance mutations in 16S and 23S ribosomal RNA genes of *Escherichia coli*. Nucl Acids Res. 12: 4653-4663. |
| 23S | 2058 | A to C | Clr-R | *Helicobacter pylori* | Stone, G. G., D. Shortridge, R. K. Flamm, J. Versalovic, J. Beyer, K. Idler, L. Zulawinski, and S. K. Tanaka. 1996. Identification of a 23S rRNA gene mutation in clarithromycin-resistant *Helicobacter pylori*. *Helicobacter*. 1: 227-228. |
| 23S | 2058 | A to C | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2058 | A to C | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to C | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2058 | A to G | Cla-R | *Helicobacter pylori* | Versalovic, J., D. Shortridge, K. Kibler, M. V. Griffy, J. Beyer, R. K. Flamm, S. K. Tanaka, D. Y. Graham, and M. F. Go. 1996. Mutations in 23S rRNA are associated with clarithromycin resistance in *Helicobacter pylori*. Antimicrob. Agents Chemother. 40: 4 |
| 23S | 2058 | A to G | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2058 | A to G | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to G | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2058 | A to U | MLSB-R | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2058 | A to U | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2058 | A to G | Clr-R | *Mycobacterium abscessus* | Wallace, R. J., Jr., A. Meier, B. A. Brown, Y. Zhang, P. Sander, G. O. Onyi, and E. C. Böttger. 1996. Genetic basis for clarithromycin resistance amoung isolates of *Mycobacterium chelonae* and *Mycobacterium abscessus*. Antimicrob. Agents Chemother. 40: 1676 |
| 23S | 2058 | A to C/G/U | Clr-R | *Mycobacterium avium* | Nash, K. A., and C. B. Inderlied. 1995. Genetic basis of macrolide resistance in *Mycobacterium avium* isolated from patients with disseminated disease. Antimicrob. Agents Chemother. 39: 2625-2630. |
| 23S | 2058 | A to C/G/U | Clr-R | *Mycobacterium avium* | Nash, K. A., and C. B. Inderlied. 1995. Genetic basis of macrolide resistance in *Mycobacterium avium* isolated from patients with disseminated disease. Antimicrob. Agents Chemother. 39: 2625-2630. |
| 23S | 2058 | A to C/G | Clr-R | *Mycobacterium chelonae* | Wallace, R. J., Jr., A. Meier, B. A. Brown, Y. Zhang, P. Sander, G. O. Onyi, and E. C. Böttger. 1996. Genetic basis for clarithromycin resistance among isolates of *Mycobacterium chelonae* and *Mycobacterium abscessus*. Antimicrob. Agents Chemother. 40: 1676 |
| 23S | 2058 | A to C/G/U | Clr-R | *Mycobacterium intracellulare* | Meier, A., P. Kirschner, B. Springer, V. A. Steingrube, B. A. Brown, R. J. Wallace, Jr., and E. C. Böttger. 1994. Identification of mutations in 23S rRNA gene of clarithromycin-resistant *Mycobacterium intracellulare*. Antimicrob. Agents Chemother. 38: 38 |
| 23S | 2058 | A to U | Clr-R | *Mycobacterium kansasii* | Burman, W. J., B. L. Stone, B. A. Brown, R. J. Wallace, Jr., and E. C. Böttger. 1998. AIDS-related *Mycobacterium kansasii* infection with initial resistance to clarithromycin. Diagn. Microbiol. Infect. Dis. 31: 369-371. |
| 23S | 2058 | A to G | Clr-R | *Mycobacterium smegmatis* | Sander, P., T. Prammananan, A. Meier, K. Frischkorn, and E. C. Böttger. 1997. The role of ribosomal RNAs in macrolide resistance. Mol. Microbiol. 26: 469-480. |
| 23S | 2058 | A to G | Ery-HR, Spi-MR, Tyl-S, Lin-HR | *Mycoplasma pneumoniae* | Lucier, T. S., K. Heitzman, S. K. Liu, and P. C. Hu. 1995. Transition mutations in the 23S rRNA of erythromycin-resistant isolates of *Mycoplasma pneumoniae*. Antimicrob. Agents Chemother. 39: 2770-2773. |
| 23S | 2058 | A to G | MLSB-R | *Propionibacteria* | Ross, J. I., E. A. Eady, J. H. Cove, C. E. Jones, A. H. Ratyal, Y. W. Miller, S. Vyakrnam, and W. J. Cunliffe. 1997. Clinical resistance to erythromycin and clindamycin in cutaneous *propionibacteria* isolated from acne patients is associated with mutatio |
| 23S | 2058 | A to G | MLSB-R | *Streptococcus pneumoniae* | Tait-Kamradt, A., T. Davies, M. Cronan, M. R. Jacobs, P. C. Appelbaum, and J. Sutcliffe. 2000. Mutations in 23S rRNA and L4 ribosomal protein account for resistance in Pneumococcal strains selected in vitro by macrolide passage. Antimicrobial Agents and |
| 23S | 2058 | A to G | MLSB-R | *Streptomyces ambofaciens* | Pernodet, J. L., F. Boccard, M. T. Alegre, M. H. Blondelet-Rouault, and M. Guérineau. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| | | | | | 1988. Resistance to macrolides, lincosamides and streptogramin type B antibiotics due to a mutation in an rRNA operon of *Streptomyces ambofaciens*. EMBO J. 7: 277-282. |
| 23S | 2058 | A to G | Ery-R | *Saccharomyces cerevisiae* mit. | Sor, F., and H. Fukuhara. 1982. Identification of two erythromycin resistance mutations in the mitochondrial gene coding for the large ribosomal RNA in yeast. Nucleic Acids Res. 10: 6571-6577. |
| 23S | 2058 | A to G | Ery-R | *Treponema pallidum* | Stamm, L. V., and H. L. Bergen. 2000. A point mutation associated with bacterial macrolide resistance is present in both 23S rRNA genes of an erythromycin-resistant *Treponema pallidum* clinical isolate [letter]. Antimicrob Agents Chemother. 44: 806-807. |
| 23S | 2059 | "A to G" | Clarithomycin resistance. | *Helecobacter pylori* | Versalovic, J., Shortridge, D., Kibler, K., Griffy, M. V., Beyer, J., Flamm, R. K., Tanaka, S. K., Graham, D. Y., and Go, M. F. (1996) Antimicrob. Agents and Chemother. 40, 477-480. |
| 23S | 2059 | "A to G" | Lincomycin resistance. | Tobacco chloroplasts | Cseplö, A., Etzold, T., Schell, J., and Schreier, P. H. (1988) Mol. Genet. 214, 295-299. |
| 23S | 2059 | "A to C" | Conferred resistance to the MLS drugs and chloramphenicol. | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2059 | "A to G" | Like A2059C | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2059 | "A to U" | Like A2059C | *E. coli* | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2059 | A to C | Mac-R, Lin-R, SB-S | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2059 | A to C | Clr-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |
| 23S | 2059 | A to G | Clr-R | *Helicobacter pylori* | Versalovic, J., D. Shortridge, K. Kibler, M. V. Griffy, J. Beyer, R. K. Flamm, S. K. Tanaka, D. Y. Graham, and M. F. Go. 1996. Mutations in 23S rRNA are associated with clarithromycin resistance in *Helicobacter pylori*. Antimicrob. Agents Chemother. 40: 4 |
| 23S | 2059 | A to G | Mac-R, Lin-R | *Helicobacter pylori* | Occhialini, A., M. Urdaci, F. Doucet-Populaire, C. M. Bébéar, H. Lamouliatte, and F. Mégraud. 1997. Macrolide resistance in *Helicobacter pylori*: rapid detection of point mutations and assays of macrolide binding to ribosomes. Antimicrob. Agents Chemothe |
| 23S | 2059 | A to G | Mac-R, Lin-R, SB-S | *Helicobacter pylori* | Wang, G., and D. E. Taylor. 1998. Site-specific mutations in the 23S rRNA gene of *Helicobacter pylori* confer two types of resistance to macrolide-lincosamide-streptogramin B antibiotics. Antimicrob. Agents Chemother. 42: 1952-1958. |
| 23S | 2059 | A to G | Cla-R | *Helicobacter pylori* | Debets-Ossenkopp, Y. J., A. B. Brinkman, E. J. Kuipers, C. M. Vandenbroucke-Grauls, and J. G. Kusters. 1998. Explaining the bias in the 23S rRNA gene mutations associated with clarithromycin resistance in clinical isolates of *Helicobacter pylori*. Antimi |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2059 | A to C/G | Clr-R | Mycobacterium abscessus | Wallace, R. J., Jr., A. Meier, B. A. Brown, Y. Zhang, P. Sander, G. O. Onyi, and E. C. Böttger. 1996. Genetic basis for clarithromycin resistance among isolates of Mycobacterium chelonae and Mycobacterium abscessus. Antimicrob. Agents Chemother. 40: 1676 |
| 23S | 2059 | A to G | Clr-R | Mycobacterium chelonae | Wallace, R. J., Jr., A. Meier, B. A. Brown, Y. Zhang, P. Sander, G. O. Onyi, and E. C. Böttger. 1996. Genetic basis for clarithromycin resistance among isolates of Mycobacterium chelonae and Mycobacterium abscessus. Antimicrob. Agents Chemother. 40: 1676 |
| 23S | 2059 | A to C | Clr/Azm-R | Mycobacterium intracellulare | Meier, A., P. Kirschner, B. Springer, V. A. Steingrube, B. A. Brown, R. J. Wallace, Jr., and E. C. Böttger. 1994. Identification of mutations in 23S rRNA gene of clarithromycin-resistant Mycobacterium intracellulare. Antimicrob. Agents Chemother. 38: 38 |
| 23S | 2059 | A to C | Clr/Azm-R | Mycobacterium avium | Meier, A., P. Kirschner, B. Springer, V. A. Steingrube, B. A. Brown, R. J. Wallace, Jr., and E. C. Böttger. 1994. Identification of mutations in 23S rRNA gene of clarithromycin-resistant Mycobacterium intracellulare. Antimicrob. Agents Chemother. 38: 38 |
| 23S | 2059 | A to G | Clr-R | Mycobacterium smegmatis | Sander, P., T. Prammananan, A. Meier, K. Frischkorn, and E. C. Böttger. 1997. The role of ribosomal RNAs in macrolide resistance. Mol. Microbiol. 26: 469-480. |
| 23S | 2059 | A to G | Ery-MR, Spi-HR, Tyl-LR, Lin-MR | Mycoplasma pneumoniae | Lucier, T. S., K. Heitzman, S. K. Liu, and P. C. Hu. 1995. Transition mutations in the 23S rRNA of erythromycin-resistant isolates of Mycoplasma pneumoniae. Antimicrob. Agents Chemother. 39: 2770-2773. |
| 23S | 2059 | A to G | Mac-R | Streptococcus pneumoniae | Tait-Kamradt, A., T. Davies, M. Cronan, M. R. Jacobs, P. C. Appelbaum, and J. Sutcliffe. 2000. Mutations in 23S rRNA and L4 ribosomal protein account for resistance in Pneumococcal strains selected in vitro by macrolide passage. Antimicrobial Agents and |
| 23S | 2059 | A to G | Mac-HR, Lin-LR | Propionibacteria | Ross, J. I., E. A. Eady, J. H. Cove, C. E. Jones, A. H. Ratyal, Y. W. Miller, S. Vyakrnam, and W. J. Cunliffe. 1997. Clinical resistance to erythromycin and clindamycin in cutaneous propionibacteria isolated from acne patients is associated with mutatio |
| 23S | 2060 | "A to C" | | E. coli | Vester, B. and Garrett, R. A. (1988) EMBO J. 7, 3577-3587. |
| 23S | 2061 | "G to A" | Chloramphenicol resistance | Rat mitochondria | Vester, B. and Garrett, R. A. (1988) EMBO J. 7, 3577-3587. |
| 23S | 2062 | "A to C" | Chloramphenicol resistance. | Halobacterium halobium | Mankin, A. S. and Garrett, R. A. (1991) J. Bacteriol. 173, 3559-3563. |
| 23S | 2251 | "G to A" | Dominant lethal; Abolished both binding of tRNA and peptidyl transferase activity. | E. coli | Green, R., Samaha, R., and Noller, H. (1997). J. Mol. Biol. 266, 40-50. |
| 23S | 2251 | "G to A" | Dominant lethal; subunit association defect. | E. coli | Gregory, S. T. and Dahlberg, A. E. (unpublished). |
| 23S | 2251 | "G to C" | Dominant lethal subunit association defect. | E. coli | Gregory, S. T. and Dahlberg, A. E. (unpublished). |
| 23S | 2251 | "G to U" | Dominant lethal subunit association defect. | E. coli | Gregory, S. T. and Dahlberg, A. E. (unpublished). |
| 23S | 2251 | "G to U" | Dominant lethal; Abolished both binding of tRNA | E. coli | Green, R., Samaha, R., and Noller, H. (1997). J. Mol. Biol. 266, 40-50. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2251 | "G to A" | and peptidyl transferase activity. Dominant lethal; impairs peptidyl transferase activity; induces DMS reactivity; induces kethoxal reactivity in G2238, G2409, G2410, G2529, and G2532; enhances CMCT reactivity in G2238; induces kethoxal and CMCT reactivity in G2269 and G2271; induces CMCT reactivity in U2272 and U2408; enhances kethoxal reactivity in G2253. | E. coli | Gregory S T, Dahlberg A E, 1999. Mutations in the Conserved P Loop Perturb the Conformation of Two Structural Elements in the Peptidyl Transferase Center of 23 S Ribosomal RNA. J. Mol. Biol. 285: 1475-1483. |
| 23S | 2252 | "G to A" | Less than 5% of control level peptidyl transferase activity. | E. coli | Porse, B. T., Thi-Ngoc, H. P., and Garrett, R. A. (1996) J. Mol. Biol. 264: 472-486. |
| 23S | 2252 | "G to C" | Less than 5% of control level peptidyl transferase activity. | E. coli | Porse, B. T., Thi-Ngoc, H. P., and Garrett, R. A. (1996) J. Mol. Biol. 264: 472-486. |
| 23S | 2252 | "G to U" | Less than 5% of control level peptidyl transferase activity. | E. coli | Porse, B. T., Thi-Ngoc, H. P., and Garrett, R. A. (1996) J. Mol. Biol. 264: 472-486. |
| 23S | 2252 | "G to C" | Reduced rate of peptidyl transferase bond formation in vitro; severely detrimental to cell growth. Double mutation (G2252C/G2253C). | E. coli | 1. Lieberman, K. R. and Dahlberg, A. E. (1994) J. Biol. Chem. 269, 16163-16169. 2. Samaha, R. R., Green R., and Noller, H. F. (1995) Nature 377, 309-314. 3. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Cell Biol. 73, 859-868. |
| 23S | 2252 | "G to A" | Severely detrimental to cell growth; promoted frameshifting and readthrough of nonsense codons. | E. coli | 1. Gregory, S. T., Lieberman, K. R., and Dahlberg, A. E. (1994) Nucleic Acids Res. 22, 279-284. 2. Lieberman, K. R. and Dahlberg, A. E. (1994) J. Biol. Chem. 269, 16163-16169. |
| 23S | 2252 | "G to C" | Severely detrimental to cell growth; promoted frameshifting and readthrough of nonsense codons. | E. coli | 1. Gregory, S. T., Lieberman, K. R., and Dahlberg, A. E. (1994) Nucleic Acids Res. 22, 279-284. 2. Lieberman, K. R. and Dahlberg, A. E. (1994) J. Biol. Chem. 269, 16163-16169. |
| 23S | 2252 | "G to U" | Severely detrimental to cell growth; promoted frameshifting and readthrough of nonsense codons. | E. coli | 1. Gregory, S. T., Lieberman, K. R., and Dahlberg, A. E. (1994) Nucleic Acids Res. 22, 279-284. 2. Lieberman, K. R. and Dahlberg, A. E. (1994) J. Biol. Chem. 269, 16163-16169. |
| 23S | 2252 | "G to A" | Dominant lethal; impairs peptidyl transferase activity; induces DMS reactivity; induces kethoxal reactivity in G2238, G2409, G2410, G2529, and G2532; enhances CMCT reactivity in G2238; induces kethoxal and CMCT reactivity in G2269 and G2271; induces | E. coli | Gregory S T, Dahlberg A E, 1999. Mutations in the Conserved P Loop Perturb the Conformation of Two Structural Elements in the Peptidyl Transferase Center of 23 S Ribosomal RNA. J. Mol. Biol. 285: 1475-1483. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| | | | CMCT reactivity in U2272 and U2408; enhances kethoxal reactivity in G2253. | | |
| 23S | 2252 | "G to A" | Interfere with the building of peptidyl-tRNA to P site of 50S subunit. | E. coli | Bocchetta M, Xiong L, Mankin A S. 1998. 23S rRNA positions essential for tRNA binding in ribosomal functional sites. Proc. Natl. Acad. Sci. 95: 3525-3530. |
| 23S | 2252 | "G to C" | Interferes with the binding of peptidyl-tRNA to P site of 50S subunit | E. coli | Bocchetta M, Xiong L, Mankin A S. 1998. 23S rRNA positions essential for tRNA binding in ribosomal functional sites. Proc. Natl. Acad. Sci. 95: 3525-3530. |
| 23S | 2252 | "G to U" | Interferes with the binding of peptidyl-tRNA to P site of 50S subunit | E. coli | Bocchetta M, Xiong L, Mankin A S. 1998. 23S rRNA positions essential for tRNA binding in ribosomal functional sites. Proc. Natl. Acad. Sci. 95: 3525-3530. |
| 23S | 2252 | "G to U" | Dominant lethal; suppressed AcPhe-Phe formation; suppressed peptide bond formation. c | E. coli | Nitta I, Ueda T, Watanabe K. 1998. Possible involvement of Escherichia coli 23S ribosomal RNA in peptide bond formation. RNA 4: 257-267. |
| 23S | 2253 | "G to C" | 42% control level peptidyl transferase activity. | E. coli | Porse, B. T., Thi-Ngoc, H. P., and Garrett, R. A. (1996) J. Mol. Biol. 264: 472-486. |
| 23S | 2253 | "G to C" | Slow growth rate. | E. coli | Gregory, S. T., Lieberman, K. R., and Dahlberg, A. E. (1994) Nucleic Acids Res. 22, 279-284. |
| 23S | 2253 | "G to C" | Promoted frameshifting and readthrough of nonsense codons. | E. coli | 1. Lieberman, K. R. and Dahlberg, A. E. (1994) J. Biol. Chem. 269, 16163-16169. 2. Samaha, R. R., Green R., and Noller, H. F. (1995) Nature 377, 309-314. 3. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Cell Biol. 73, 859-868. |
| 23S | 2253 | "G to A" | Promoted frameshifting and readthrough of nonsense codons. | E. coli | 1. Lieberman, K. R. and Dahlberg, A. E. (1994) J. Biol. Chem. 269, 16163-16169. 2. Samaha, R. R., Green R., and Noller, H. F. (1995) Nature 377, 309-314. 3. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Cell Biol. 73, 859-868. |
| 23S | 2253 | "G to U" | Promoted frameshifting and readthrough of nonsense codons. | E. coli | 1. Lieberman, K. R. and Dahlberg, A. E. (1994) J. Biol. Chem. 269, 16163-16169. 2. Samaha, R. R., Green R., and Noller, H. F. (1995) Nature 377, 309-314. 3. O'Connor, M., Brunelli, C. A., Firpo, M. A., Gregory, S. T., Lieberman, K. R., Lodmell, J. S., Moline, H., Van Ryk, D. I., and Dahlberg, A. E. (1995) Cell Biol. 73, 859-868. |
| 23S | 2253 | "G to A" | 19% of control level peptidyl transferase activity. | E. coli | Porse, B. T., Thi-Ngoc, H. P., and Garrett, R. A. (1996) J. Mol. Biol. 264: 472-486. |
| 23S | 2253 | "G to C" | Severely detrimental to cell growth; reduced rate of peptide bond formation in vitro. Double mutations (C2253C/2252C). | E. coli | 1. Lieberman, K. R. and Dahlberg, A. E. (1994) J. Biol. Chem. 269, 16163-16169. 2. Samaha, R. R., Green R., and Noller, H. F. (1995) Nature 377, 309-314. 3. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Cell Biol. 73, 859-868. |
| 23S | 2253 | "G to U" | Less than 5% control level peptidyl transferase activity. | E. coli | Porse, B. T., Thi-Ngoc, H. P., and Garrett, R. A. (1996) J. Mol. Biol. 264: 472-486. |
| 23S | 2253 | "G to A" | Induced DMS reactivity; enhanced CMCT reactivity in G2238; induced kethoxal and CMCT reactivity in G2269 and G2271; induced CMCT reactivity in U2272; induced | E. coli | Gregory S T, Dahlberg A E, 1999. Mutations in the Conserved P Loop Perturb the conformation of Two Structural Elements in the Peptidyl Transferase center of 23 S Ribosomal RNA. J. Mol. Biol. 285: 1475-1483. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2253 | "G to C" | kethoxal reactivity in G2409 and G2410. Induced DMS reactivity; enhanced CMCT reactivity in G2238; induced kethoxal and CMCT reactivity in G2269 and G2271; induced CMCT reactivity in U2272; induced kethoxal reactivity in G2409 and G2410. | *E. coli* | Gregory S T, Dahlberg A E, 1999. Mutations in the Conserved P Loop Perturb the Conformation of Two Structural Elements in the Peptidyl Transferase Center of 23 S Ribosomal RNA. J. Mol. Biol. 285: 1475-1483. |
| 23S | 2438 | "U to A" | Amicetin resistance and reduced growth rate. | *Halobacterium halobium* | Leviev, I. G., Rodriguez-Fonseca, C., Phan, H., Garrett, R. A., Heliek, G., Noller, H. F., and Mankin, A. S (1994) EMBO J. 13, 1682-1686. |
| 23S | 2438 | "U to C" | Amicetin resistance. | *Halobacterium halobium* | Leviev, I. G., Rodriguez-Fonseca, C., Phan, H., Garrett, R. A., Heliek, G., Noller, H. F., and Mankin, A. S (1994) EMBO J. 13, 1682-1686. |
| 23S | 2438 | "U to G" | Unstable in presence or absence of amicetin | *Halobacterium halobium* | Leviev, I. G., Rodriguez-Fonseca, C., Phan, H., Garrett, R. A., Heliek, G., Noller, H. F., and Mankin, A. S (1994) EMBO J. 13, 1682-1686. |
| 23S | 2447 | "G to A" | Chloramphenicol resistance. | Yeast mitochondria | Dujon, B. (1980) Cell 20, 185-197. |
| 23S | 2447 | "G to C" | Anisomycin resistance. | *Halobacterium halobium* | Hummel, H. and Böck, A. (1987) Biochimie 69, 857-861. |
| 23S | 2450 | "A to C" | Lethal. | *E. coli* | Vester, B. and Garrett, R. A. (1988) EMBO J. 7, 3577-3587. |
| 23S | 2451 | "A to U" | Chloramphenicol resistance. | Mouse mitochondria | Kearsey, S. E. and Craig, I. W. (1981) Nature (London) 290: 607-608. |
| 23S | 2451 | "A to G" | Like A2451G | *E. coli* | Bocchetta M, Xiong L, Mankin A S. 1998. 23S rRNA positions essential for tRNA binding in ribosomal functional sites. Proc. Natl. Acad. Sci. 95: 3525-3530. |
| 23S | 2451 | "A to C" | Like A2451G | *E. coli* | Bocchetta M, Xiong L, Mankin A S. 1998. 23S rRNA positions essential for tRNA binding in ribosomal functional sites. Proc. Natl. Acad. Sci. 95: 3525-3530. |
| 23S | 2452 | "C to A" | Chloramphenicol resistance. | Human mitochondria | Blanc, H., Wright C. T., Bibb M. J., Wallace D. C., and Clayton D. A. (1981) Proc. Natl. Acad. Sci. USA 78, 3789-3793. |
| 23S | 2452 | "C to U" | Animosycin resistance. | *Halobacterium* | Hummel, H. and Böck, A. (1987) Biochimie 69, 857-861. |
| 23S | 2452 | "C to U" | Animosycin resistance | *Tetrahymena thermophilia* | Sweeney, R., Yao, C. H., and Yao, M. C. (1991) Genetics 127: 327-334. |
| 23S | 2452 | "C to U" | Chloramphenicol resistance. | *Halobacterium halobium* | Mankin, A. S. and Garrett, R. A. (1991) J. Bacteriol. 173: 3559-3563. |
| 23S | 2452 | "C to U" | Chloramphenicol resistance | Mouse mitochondria | Slott, E. F., Shade R. O., and Lansman, R. A. (1983) Mol. Cell. Biol. 3, 1694-1702. |
| 23S | 2452 | "C to U" | Low level sparsomycin resistance | *Halobacterium halobium* | Tan, G. T., DeBlasio, A., and Mankin, A. S. (1996) J. Mol. Biol. 261, 222-230. |
| 23S | 2452 | C to U | Cbm-R, Lin-R | *Sulfolobus acidocaldarius* | Aagaard, C., H. Phan, S. Trevisanato, and R. A. Garrett. 1994. A spontaneous point mutation in the single 23S rRNA gene of the thermophilic arachaeon *Sulfolobus acidocaldarius* confers multiple drug resistance. J. Bacteriol. 176: 7744-7747. |
| 23S | 2453 | "A to C" | Anisomycin resistance | *Halobacterium halobium* | Hummel, H. and Böck, A. (1987) Biochimie 69, 857-861. |
| 23S | 2492 | "U to A" | Frameshift suppressors. | *E. coli* | O'Connor, M. and Dahlberg, A. E. (1996) Nucleic Acids Res. 24, 2701-2705. |
| 23S | 2492 | "U to C" | Frameshift suppressors. | *E. coli* | O'Connor, M. and Dahlberg, A. E. (1996) Nucleic Acids Res. 24, 2701-2705. |
| 23S | 2493 | "del U" | (With A2058G and erythromycin) Lethal growth effects. Frameshift suppressors. | *E. coli* | O'Connor, M. and Dahlberg, A. E. (1996) Nucleic Acids Res. 24, 2701-2705. |
| 23S | 2493 | "U to A" | (With A2058G and erythromycin) Lethal growth effects. | *E. coli* | 1. Porse, B. T. and Garrett, R. A. (1995) J. Mol. Biol. 249, 1-10. 2. O'Connor, M., Brunelli, C. A., Firpo, M. A., Gregory, S. T., |

TABLE 3-continued

Compilation of antibiotic resistance due to mutations on the 23S rRNA

| Type of RNA | Position | Alteration(s) | Phenotype | Organism | Reference |
|---|---|---|---|---|---|
| | | | Frameshift suppressors | | Lieberman, K. R., Lodmell, J. S., Moine, H., Van Ryk, D. I., and Dahlberg, A. E. (1995) Biochem. Cell Biology 73, 859-868. |
| 23S | 2493 | "U to C" | (With A2058G and erythromycin) Lethal growth effects. Frameshift suppressors | E. coli | 1. Porse, B. T. and Garrett, R. A. (1995) J. Mol. Biol. 249, 1-10. 2. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Biochem. Cell Biology 73, 859-868. 3. O'Connor, M. and Dahlberg, A. E. (1996) Nucleic Acids Res. 24, 2701-2705 |
| 23S | 2493 | "U to C" | (With A2058G and erythromycin) Lethal growth effects. Frameshift suppressors | E. coli | O'Connor, M. and Dahlberg, A. E. (1996) Nucleic Acids Res. 24, 2701-2705 |
| 23S | 2493 | "U to G" | (With A2058G and erythromycin) Lethal growth effects. Frameshift suppressors | E. coli | O'Connor, M. and Dahlberg, A. E. (1996) Nucleic Acids Res. 24, 2701-2705 |
| 23S | 2493 | "U to A" | (With A2058G and erythromycin) Lethal growth effects. Frameshift suppressors | E. coli | O'Connor, M. and Dahlberg, A. E. (1996) Nucleic Acids Res. 24, 2701-2705 |
| 23S | 2493 | "U to C" | Increased misreading. Double mutation (U2493C/G2458A) | E. coli | O'Connor, M. and Dahlberg, A. E. (1996) Nucleic Acids Res. 24, 2701-2705 |
| 23S | 2493 | "U to C" | Increased misreading. Double mutation (U2493C/G2458C) | E. coli | O'Connor, M. and Dahlberg, A. E. (1996) Nucleic Acids Res. 24, 2701-2705 |
| 23S | 2497 | "A to G" | (With A2058G and erythromycin) Reduced growth rate. | E. coli | Porse, B. T. and Garrett, R. A. (1995) J. Mol. Biol. 249, 1-10. |
| 23S | 2499 | "C to U" | Sparsomycin resistance | Halobacterium halobium | Tan, G. T., DeBlasio, A. and Mankin, A. S. (1996) J. Mol. Biol. 261, 222-230 |
| 23S | 2500 | U2500A/C2501A | Inhibits binding of 1A streptogramin B, antibiotic pristinamycin 1A on peptidyl transferase loop causing inhibition of peptide elongation. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500A/C2501G | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500A/C2501U | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500G/C2501A | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500G/C2501G | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500G/C2501U | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500C/C2501A | Like U2500A/C2501A. c | E. coli | Porse B T, Garrett R A. 1999. Sites of Interaction of Streptogramin A and B Antibiotics in the Peptidyl Transferase |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2500 | U2500C/C2501G | Like U2500A/C2501A. c. | E. coli | Loop of 23 S rRNA and the Synergism of their Inhibitory Mechanisms. J. Mol. Biol. 286: 375-387. Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2500 | U2500C/C2501A | Like U2500A/C2501A. c | E. coli | Porse B T, Garrett R A. 1999. Sites of Interaction of Streptogramin A and B Antibiotics in the Peptidyl Transferase Loop of 23 S rRNA and the Synergism of their Inhibitory Mechanisms. J. Mol. Biol. 286: 375-387. |
| 23S | 2502 | "G to A" | Decreased growth rate | E. coli | Vester, B. and Garrett, R. A. (1988) EMBO J. 7, 3577-3587 |
| 23S | 2503 | "A to C" | Chloramphenicol resistance | Yeast mitochondria | Dujon, B. (1980) Cell 20, 185-197 |
| 23S | 2503 | "A to C" | Decreased growth rate; CAMr | E. coli | Porse, B. T. and Garrett, R. A. (1995) J. Mol. Biol. 249, 1-10. |
| 23S | 2503 | "A to G" | (With A2058G and erythromycin) Slow growth rate. CAMr | E. coli | Porse, B. T. and Garrett, R. A. (1995) J. Mol. Biol. 249, 1-10. |
| 23S | 2504 | "U to A" | Increased readthrough of stop codons and frameshifting; lethal | E. coli | O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Biochem. Cell Biology 73, 859-868. |
| 23S | 2504 | "U to C" | Increased readthrough of stop codons and frameshifting; lethal | E. coli | O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Biochem. Cell Biology 73, 859-868. |
| 23S | 2504 | "U to C" | Chloramphenicol resistance | Mouse mitochondria | Blanc, H., Wright, C. T., Bibb, M. J., Wallace, D. C., and Clayton, D. A. (1981) Proc. Natl. Acad. Sci. USA 78, 3789-3793 |
| 23S | 2504 | "U to C" | Chloramphenicol resistance | Human mitochondria | Kearsey, S. E., and Craig, I. W. (1981) Nature (London) 290, 607-608 |
| 23S | 2505 | "G to A" | 14% activity of 70S ribosomes | E. coli | Porse, B. T., Thi-Ngoc, H. P. and Garrett, R. A. (1996) J. Mol. Biol. 264, 472-486 |
| 23S | 2505 | "G to C" | (With A1067U and thiostrepton) Temperature sensitive growth. a Hypersensitivity to CAM; increased sensitivity of in vitro translation. Slight increase in sensitivity to lincomycin. b No effect on translational accuracy. | E. coli | 1. Saarma, U. and Remme, J. (1992) Nucleic Acids Res. 23, 2396-2403. 2. Saarma, U., Lewicki, B. T. U., Margus, T., Nigul, S., and Remme, J. (1993) "The Translational Apparatus: Structure, Function, Regulation and Evolution" 163-172. |
| 23S | 2505 | "G to C" | Excluded from 70S ribosomes; 17% activity of 70S ribosomes | E. coli | Porse, B. T., Thi-Ngoc, H. P. and Garrett, R. A. (1996) J. Mol. Biol. 264, 472-486 |
| 23S | 2505 | "G to U" | <5% activity of 70S ribosomes | E. coli | Porse, B. T., Thi-Ngoc, H. P. and Garrett, R. A. (1996) J. Mol. Biol. 264, 472-486 |
| 23S | 2505 | "G to A" | Conferred resistance to the MLS drugs and chloramphenicol. | E. coli | Hansen LH, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2505 | "G to C" | Like G2505A. | E. coli | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2505 | "G to U" | Like G2505A | E. coli | Hansen L H, Mauvais P, Douthwaite S. 1999. The macrolide-kelotide antibiotic binding site is formed by structures in domains II and V of 23S ribosomal RNA. Molecular Microbiology 31 (2): 623-631. |
| 23S | 2506 | "U to A" | Dominant lethal; 5% activity of 70S ribosomes | E. coli | Porse, B. T., Thi-Ngoc, H. P. and Garrett, R. A. (1996) J. Mol. Biol. 264, 472-486 |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2508 | "A to U" | Eryr, Cdr, Cms; abolishes methylation of 23S rRNA by ErmE. | E. coli | 1. Sigmund, C. D., Ettayebi, M., and Morgan, E. A. (1984) Nucleic Acids Res. 12, 4653-4663. 2. Vannuffel, P., Di Giambattista, M., and Cocito, C. (1992) J. Biol. Chem. 267, 16114-16120. 3. Douthwaite, S. and Aagaard, C. (1993) J. Mol. Biol. 232, 725-731. 4. Vester, B., Hansen, L. H., and Douthwaite, S. (1995) RNA 1, 501-509. |
| 23S | 2508 | "G to U" | Control level peptidyl transferase activity | E. coli | 1. Porse, B. T. and Garrett, R. A. (1995) J. Mol. Biol. 249, 1-10. 2. Porse, B. T., Thi-Ngoc, H. P. and Garrett, R. A. (1996) J. Mol. Biol. 264, 472-486 |
| 23S | 2514 | "U to C" | Control level peptidyl transferase activity | E. coli | Porse, B. T. and Garrett, R. A. (1995) J. Mol. Biol. 249, 1-10. |
| 23S | 2516 | "A to U" | Control level peptidyl transferase activity | E. coli | Porse, B. T. and Garrett, R. A. (1995) J. Mol. Biol. 249, 1-10. |
| 23S | 2528 | "U to A" | (With A2058G and erythromycin) Slow growth rate. Control level peptidyl transferase activity | E. coli | Porse, B. T. and Garrett, R. A. (1995) J. Mol. Biol. 249, 1-10. |
| 23S | 2528 | "U to C" | Control level peptidyl transferase activity | E. coli | Porse, B. T. and Garrett, R. A. (1995) J. Mol. Biol. 249, 1-10. |
| 23S | 2530 | "A to G" | (With A2058G and erythromycin) Slow growth rate. | E. coli | Porse, B. T. and Garrett, R. A. (1995) J. Mol. Biol. 249, 1-10. |
| 23S | 2546 | "U to C" | Control level peptidyl transferase activity. | E. coli | Porse, B. T. and Garrett, R. A. (1995) J. Mol. Biol. 249, 1-10. |
| 23S | 2550 | "G to A" | (With A2058G and erythromycin) Slow growth rate. | E. coli | Porse, B. T. and Garrett, R. A. (1995) J. Mol. Biol. 249, 1-10. |
| 23S | 2552 | "U to A" | (With A2058G and erythromycin) Slow growth rate. | E. coli | Porse, B. T. and Garrett, R. A. (1995) J. Mol. Biol. 249, 1-10. |
| 23S | 2555 | "U to A" | Stimulates readthrough of stop codons and frameshifting; U to A is trpE91 frameshift suppressor; viable in low copy number plasmids, but lethal when expressed constitutively from lambda pL promoter | E. coli | 1. O'Connor, M. and Dahlberg, A. E. (1993) Proc. Natl. Acad. Sci. USA 90, 9214-9218 2. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Biochem. Cell Biology 73, 859-868. |
| 23S | 2555 | "U to C" | (With A2058G and erythromycin) Slow growth rate. Control level peptidyl transferase activity | E. coli | Porse, B. T. and Garrett, R. A. (1995) J. Mol. Biol. 249, 1-10. |
| 23S | 2555 | "U to C" | no effect | E. coli | O'Connor, M. and Dahlberg, A. E. (1993) Proc. Natl. Acad. Sci. USA 90, 9214-9218 |
| 23S | 2557 | "G to A" | (With A2058G and erythromycin) Slow growth rate. Intermediate decrease in peptidyl transferase activity. | E. coli | Porse, B. T. and Garrett, R. A. (1995) J. Mol. Biol. 249, 1-10. |
| 23S | 2565 | "A to U" | (With A2058G and erythromycin) Slow growth rate. Very low peptidyl transferase activity. | E. coli | Porse, B. T. and Garrett, R. A. (1995) J. Mol. Biol. 249, 1-10. |
| 23S | 2580 | "U to C" | (With A2058G and erythromycin) Lethal growth effects. No peptidyl transferase activity. | E. coli | Porse, B. T. and Garrett, R. A. (1995) J. Mol. Biol. 249, 1-10. |
| 23S | 2581 | "G to A" | Dominant lethal inhibition of puromycin in reaction | E. coli | 1. Spahn, C., Reeme, J., Schafer, M. and Nierhaus, K. (1996) J. Biol. Chem. 271, 32849-32856 2. Spahn, C., Reeme, J., Schafer, M. and Nierhaus, K. (1996) J. Biol. Chem. 271, 32857-32862 |
| 23S | 2584 | "U to A" | Deleterious; 20% activity of 70S ribosomes | E. coli | Porse, B. T., Thi-Ngoc, H. P. and Garrett, R. A. (1996) J. Mol. Biol. 264, 472-486 |
| 23S | 2584 | "U to C" | Deleterious; 20% activity of 70S ribosomes | E. coli | Porse, B. T., Thi-Ngoc, H. P. and Garrett, R. A. (1996) J. Mol. Biol. 264, 472-486 |
| 23S | 2584 | "U to G" | (With A2058G and erythromycin) Lethal growth | E. coli | Porse, B. T. and Garrett, R. A. (1995) J. Mol. Biol. 249, 1-10. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2589 | "A to G" | effects. No peptidyl transferase activity. (With A2058G and erythromycin) Slow growth rate. Strong reduction in peptidyl transferase activity. | E. coli | Porse, B. T. and Garrett, R. A. (1995) J. Mol. Biol. 249, 1-10. |
| 23S | 2602 | A2602C/C2501A | Inhibits binding of 1A streptogramin B, antibiotic pristinamycin 1A on peptidyl transferase loop causing inhibition of peptide elongation. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602C/C2501U | Like A2602C/C2501A. c | E. coli | Porse B T, Kirillov S V, Awayez M J, Garrett RA. 1999. UV-induced modifications in the peptidyl transferase loop of 23S rRNA dependent on binding of the streptogramin B antibiotic pristinamycin IA. RNA 5: 585-595. |
| 23S | 2602 | A2602C/C2501G | Like A2602C/C2501A. c | E. coli | Porse B T, Kirillov S V, Awayez M J, Garrett RA. 1999. UV-induced modifications in the peptidyl transferase loop of 23S rRNA dependent on binding of the streptogramin B antibiotic pristinamycin IA. RNA 5: 585-595. |
| 23S | 2602 | A2602U/C2501A | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602U/C2501U | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602U/C2501G | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602G/C2501A | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602G/C2501U | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2602 | A2602G/C2501G | Like A2602C/C2501A. c | E. coli | Porse B T, Kirillov S V, Awayez M J, Garrett R A. 1999. UV-induced modifications in the peptidyl transferase loop of 23S rRNA dependent on binding of the streptogramin B antibiotic pristinamycin IA. RNA 5: 585-595. |
| 23S | 2611 | "C to G" | Erythromycin and spiramycin resistance | Chlamydomonas reinhardtii | Gauthier, A., Turmel, M. and Lemieux, C. (1988) Mol. Gen. Genet. 214, 192-197. |
| 23S | 2611 | "C to G" | Erythromycin and spiramycin resistance | Yeast mitochondria | Sor, F. and Fukahara, H. (1984) Nucleic Acids Res. 12, 8313-8318. |

TABLE 3-continued

Compilation of antibiotic resistance due to mutations on the 23S rRNA

| Type of RNA | Position | Alteration(s) | Phenotype | Organism | Reference |
|---|---|---|---|---|---|
| 23S | 2611 | "C to U" | Eryr and low level lincomycin and clindamycin resistance | *Chlamydomonas reinhardtii* | Harris, E. H., Burkhart, B. D., Gillham, N. W. and Boynton, J. E. (1989) Genetics 123, 281-292 |
| 23S | 2611 | "C to G" | Eryr and low level lincomycin and clindamycin resistance | *Chlamydomonas reinhardtii* | Harris, E. H., Burkhart, B. D., Gillham, N. W. and Boynton, J. E. (1989) Genetics 123, 281-292 |
| 23S | 2611 | "C to U" | Slightly Eryr; reduced methylation Double mutation (C2611U/G2057A) | *E. coli* | Vester, B., Hansen, L. H., and Douthwaite, S. (1995) RNA 1, 501-509 |
| 23S | 2611 | C to G | Ery-R, Spi-LR | *Chlamydomonas moewusii* chl. | Gauthier, A., M. Turmel, and C. Lemieux. 1988. Mapping of chloroplast mutations conferring resistance to antibiotics in *Chlamydomonas*: evidence for a novel site of streptomycin resistance in the small subunit rRNA. Mol. Gen. Genet. 214: 192-197. |
| 23S | 2611 | C to G/U | Ery-R, Lin-MR | *Chlamydomonas reinhardtii* chl. | Harris, E. H., B. D. Burkhart, N. W. Gillham, and J. E. Boynton. 1989. Antibiotic resistance mutations in the chloroplast 16S and 23S rRNA genes of *Chlamydomonas reinhardtii*: correlation of genetic and physical maps of the chloroplast genome. Genetics. |
| 23S | 2611 | C to U | Ery-R, Spi-S, Tyl-S, Lin-S | *Escherichia coli* | Vannuffel, P., M. Di Giambattista, E. A. Morgan, and C. Cocito. 1992. Identification of a single base change in ribosomal RNA leading to erythromycin resistance. J. Biol. Chem. 267: 8377-8382. |
| 23S | 2611 | C to A/G | Mac-R, SB-S | *Streprococcus pneumoniae* | Tait-Kamradt, A., T. Davies, M. Cronan, M. R. Jacobs, P. C. Appelbaum, and J. Sutcliffe. 2000. Mutations in 23S rRNA and L4 ribosomal protein account for resistance in Pneumococcal strains selected in vitro by macrolide passage. Antimicrobial Agents and |
| 23S | 2611 | C to G | Ery-R, Spi-R | *Saccharomyces cerevisiae* mit. | Sor, F., and H. Fukuhara. 1984. Erythromycin and spiramycin resistance mutations of yeast mitochondria: nature of the rib2 locus in the large ribosomal RNA gene. Nucleic Acids Res. 12: 8313-8318. |
| 23S | 2611 | C to U | Ery-S, Spi-R | *Saccharomyces cerevisiae* mit. | Sor, F., and H. Fukuhara. 1984. Erythromycin and spiramycin resistance mutations of yeast mitochondria: nature of the rib2 locus in the large ribosomal RNA gene. Nucleic Acids Res. 12: 8313-8318. |
| 23S | 2661 | "G to C" | Decreased misreading; streptomycin dependent when expressed with Smr, hyperaccurate S12 mutation. | *E. coli* | 1. Tapprich, W. E. and Dalhberg, A. E. (1990) EMBO J. 9, 2649-2655 2. Tapio, S. and Isaksson, L. A. (1991) Eur. J. Biochem. 202, 981-984 3. Melancon, P., Tapprich, W. and Brakier-Gingras, L. (1992) J. Bacteriol. 174, 7896-7901 4. Bilgin, N. and Ehrenberg, M. (1994) J. Mol. Biol. 235, 813-824 5. O'Connor, M., Brunelli, C. A., Firpo, M. A., Gregory, S. T., Lieberman, K. R., Lodmell, J. S., Moine, H., Van Ryk, D. I., and Dahlberg, A. E. (1995) Biochem. Cell Biology 73, 859-868. |
| 23S | 2661 | "C to A" | Like C2661 | *E. coli* | Munishkin A, Wool IG. 1997. The ribosome-in-pieces: Binding of elongation factor EF-G to oligoribonucleotides that mimic the sarcin/ricin and thiostrepton domains of 23S ribosomal RNA. Proc. Natl. Acad. Sci. 94: 12280-12284. |
| 23S | 2661 | "C to G" | Like C2661 | *E. coli* | Munishkin A, Wool IG. 1997. The ribosome-in-pieces: Binding of elongation factor EF-G to |

TABLE 3-continued

Compilation of antibiotic resistance due to mutations on the 23S rRNA

| Type of RNA | Position | Alteration(s) | Phenotype | Organism | Reference |
|---|---|---|---|---|---|
| | | | | | oligoribonucleotides that mimic the sarcin/ricin and thiostrepton domains of 23S ribosomal RNA. Proc. Natl. Acad. Sci. 94: 12280-12284. |
| 23S | 2661 | "C to U" | Like C2661 | E. coli | Munishkin A, Wool IG. 1997. The ribosome-in-pieces: Binding of elongation factor EF-G to oligoribonucleotides that mimic the sarcin/ricin and thiostrepton domains of 23S ribosomal RNA. Proc. Natl. Acad. Sci. 94: 12280-12284. |
| 23S | 2666 | "C to G" | Increased stop codon readthrough and frameshifting. a Double mutation (C2666G/A2654C) | E. coli | O'Connor, M. and Dalhberg, A. E. (1996) Nucleic Acids Res. 24, 2701-2705 |
| 23S | 2666 | "C to G" | Minor increase in stop codon readthrough and frameshifting. a Double mutation (C2666G/A2654U) | E. coli | O'Connor, M. and Dalhberg, A. E. (1996) Nucleic Acids Res. 24, 2701-2705 |
| 23S | 2666 | "C to U" | Minor increase in stop codon readthrough and frameshifting. a Double mutation (C2666U/A2654C) | E. coli | O'Connor, M. and Dalhberg, A. E. (1996) Nucleic Acids Res. 24, 2701-2705 |
| 23S | 2666 | "C to U" | Significant increase in stop codon readthrough and frameshifting. a Double mutation (C2666U/A2654G) | E. coli | O'Connor, M. and Dalhberg, A. E. (1996) Nucleic Acids Res. 24, 2701-2705 |
| 23S | 2666 | "C to U" | Minor increase in stop codon readthrough and frameshifting. a Double mutation (C2666U/A2654U) | E. coli | O'Connor, M. and Dalhberg, A. E. (1996) Nucleic Acids Res. 24, 2701-2705 |

TABLE 4

| | Resistance | Pathogen | Recomended Etest | Mechanism | Effect of resistance on fluorescence | % Change in Fluorescenc |
|---|---|---|---|---|---|---|
| MRSA | Methicillin Resistant SA | Staphylococcus aureus | | Reduced affinity of PBP2 towards penicillins; nosocomial, Multi-drug-resistant (clindamycin, gentamicin, FQ); Contain SCCmec type I, II, or III; Usually PVL-negative; Virulent (esp. skin and lung) | Reduction of Penicillin binding | > to ≈80% reduction |
| CA-MRSA | Community acquired MRSA; | Staphylococcus aureus | | Multi-drug-resistant (clindamycin, gentamicin, FQ); Usually only resistant to pen, ox ± eryth ± FQs; Usually produce PVL, especially in the US; In general the organisms remain susceptible to clindamycin and to trimethoprim sulfa. That's different from a nosocomial pathogen which is usually resistant to one of these antibiotics. | Reduction of Penecillin binding. Maintaims binding capacity for clindamycin and trimethoprim | > to ≈80% reduction of penicillin, clindamycin trimethoprim binding |
| PVL-MRSA | Panton-Valentine leukocidin - MRSA | Staphylococcus aureus | | Highly abundant toxin, scausing septic shock; large complications | — | — |
| BORSA | Border.line oxacillin resistant SA | Staphylococcus aureus | Oxacillin | | Reduction of Penecillin binding. | > to ≈80% reduction of penicillin |
| ORSA | Oxacillin resistant SA | Staphylococcus aureus | Oxacillin | | Reduction of Penecillin binding. | > to ≈80% reduction of penicillin |
| VRSA | Vancomycin resistant SA | Staphylococcus aureus | Vancomycin; Teicoplanin | Modified phenotypic features, however, include slower growth rates, a thickened cell wall, and increased levels of PBP2 and PBP2' (although the degree of cross-linking within the thick cell wall seems to be reduced) [58]. Vancomycin resistant strains also seem to have a greater ability to absorb the antibiotic from the outside medium, which may be a consequence of the greater availability of stem peptides in the thick cell wall. In addition, the increased amounts of two PBPs may compete with the | Increased binding of Vancomycin | |
| VRS | Vancomycin resistant Staph | Staphylococci (CNS) | Vancomycin | | Increased binding of Vancomycin >50% | >50% |

TABLE 4-continued

| Resistance | Pathogen | Recomended Etest | Mechanism | Effect of resistance on fluorescence | % Change in Fluorescenc |
|---|---|---|---|---|---|
| | | | antibiotic for the stem peptide substrates, thus aggravating the resistance profile | | |
| VISA | Vancomycin intermediary SA | Staphylococcus aureus | Vancomycin | | Increased binding of Vancomycin 20-50% | 20-50% |
| hVISA | hetero-(resistant) Vancomycin | Staphylococcus aureus | Vancomycin | very rare, but can be susceptible to methicillin and resistant to vancomycin | Binding of penicillin and vancomycin | |
| VRE | Vancomycin resistant | Enterococci | Vancomycin; Teicoplanin | Reduced affinity to Van by 3 orders of magnitude | Reduction of vancomycin binding | >80% reduction |
| ESBL | Extended Spectrum β-Lactamase | Entero-bacteriaceae | | Overproduction of β-Lactamases, inhibited by clavulanic acid | Increased binding of clavulanic acid | >80% increase |
| ESBL | Extended Spectrum β-Lactamase | Pseudomonas spp. | Ceftazidime | Overproduction of β-Lactamases, inhibited by clavulanic acid | Increased binding of clavulanic acid | >80% increase |
| ESBL | Extended Spectrum β-Lactamase | Acinetobacter | Ceftazidime | Overproduction of β-Lactamases, inhibited by clavulanic acid | Increased binding of clavulanic acid | >80% increase |
| ESBL | Extended Spectrum β- | BCC | Ceftazidime | Overproduction of β-Lactamases, inhibited by clavulanic acid | Increased binding of clavulanic acid | >80% increase |
| ESBL | Extended Spectrum β-Lactamase | Stenotrophomonas maltophilia | Ceftazidime | Overproduction of β-Lactamases, inhibited by clavulanic acid | Increased binding of clavulanic acid | >80% increase |
| MBL | Metalo-β-Lactamase | | Imipenem | | — | — |
| MLS | macrolide lincosamide streptogramin | | | One mechanism is called MLS, macrolide lincosamide streptogramin. And in this situation there is an alteration in a target-binding site at the 23-ribosomal RNA level. resulting in a point mutation or methylation of 23SRNA resulting in reduced binding of macrolides (also Ketolides); organisms with an efflux mechanis will bind macrolides under FISH conditions. They are also sensitive to clindamycin | Reduced binding of macrolides and Ketolides | >50% |
| DRSP | drug-resistant S. pneumoniae | Modify clavulanic acid, & single gene detection for efflux pump | | DR is reported for beta-lactams, macrolides, chloramphenicol, and sulfonamides | Reduction of macrolides | >50% |
| HLAR | High level Aminoglycoside Resistance in Enterococci | Enterococci | Gentamycin; Streptomycin | | Reduction in Streptomycin binding | >80% reduction |

REFERENCES

1. Chambers, H. F. (1997). Methicillin resistance in staphylococci: molecular and biochemical basis and clinical implications. Clinical Microbiology Reviews 10, 781-791.
2. Swenson, J. M., Williams, P., Killgore, G. et al. (2001). Performance of eight methods, including two new methods for detection of oxacillin resistance in a challenge set of Staphylococcus aureus organisms. Journal of Clinical Microbiology 39, 3785-8
3. Van Leeuwen, W. B., Van Pelt, C., Luijendijk, A. et al. (1999). Rapid detection of methicillin resistance in Staphylococcus aureus isolates by the MRSA-screen latex agglutination test. Journal of Clinical Microbiology 37, 3029-30.
4. Louie, L., Majury, A., Goodfellow, J. et al. (2001). Evaluation of a latex agglutination test (MRSA-Screen) for detection of oxacillin resistance in coagulase-negative staphylococci. Journal of Clinical Microbiology 39, 4149-51.
5. Skov, R., Smyth, R., Clausen, M. et al. (2003). Evaluation of cefoxitin 30 μg disc on Iso-Sensitest agar for detection of methicillin-resistant Staphylococcus aureus. Journal of Antimicrobial Chemotherapy 52, 204-7
6. Felten, A., Grandry, B., Lagrange, P. H. et al. (2002). Evaluation of three techniques for detection of low-level methicillin-resistant S. aureus (MRSA): a disc diffusion method with cefoxitin and moxalactam, the Vitek 2 system, and the MRSA-screen latex agglutination test. Journal of Clinical Microbiology 40, 2766-71.
7. Cauwelier, B., Gordts, B., Descheemaecker, P. et al. (2004). Evaluation of a disk diffusion method with cefoxitin (30 μg) for detection of methicillin-resistant Staphylococcus aureus. European Journal of Clinical Microbiology and Infectious Diseases 23, 389-92.
8. Kluytmans, J., Van Griethuysen, A., Willemse, P. et al. (2002). Performance of CHROM agar selective medium and oxacillin resistance screening agar base for identifying Staphylococcus aureus and detecting methicillin resistance. Journal of Clinical Microbiology 40, 2480-2.
9. Louie, L., Matsumura, S. O., Choi, E. et al. (2000). Evaluation of three rapid methods for detection of methicillin resistance in S. aureus. Journal of Clinical Microbiology 38, 2170-3.
10. National Committee for Clinical Laboratory Standards. (2003). Methods for Dilution Antimicrobial Susceptibility Tests for Bacteria that Grow Aerobically: Approved Standards M7-A6 and M100-S13. NCCLS, Wayne, Pa., USA.

The invention claimed is:

1. A method for the detection of antibiotic resistance in a micro-organism in a biological sample, comprising:
   (a) providing a labelled antibiotic,
   (b) contacting the labelled antibiotic with a biological sample comprising a micro-organism under conditions which allow binding of the labeled antibiotic to its binding site in the micro-organism or to a protein secreted by the micro-organism,
   (c) detecting the labelled antibiotic in the micro-organism,
   (d) identifying the micro-organism, and
   (e) determining whether the amount of detectable label is altered with respect to the amount of detectable label in the micro-organism in its non-resistant form,
   wherein micro-organisms in which the amount of detectable label is altered with respect to the amount of detectable label in the micro-organism in its non-resistant form are microorganisms resistant against the antibiotic.

2. The method according to claim 1, wherein the antibiotic is selected from the group consisting of aminoglycosides, carbacephems, carbapenerns, cephalosporins, glycopeptides, macrolides, monobactams, beta-lactam antibiotics, quinolones, bacitracin, sulfonamides, tetracyclines, streptogramines, chloramphenicol, clindamycin, and lincosamide.

3. The method according to claim 1, wherein the antibiotic is labelled by a luminescent labelling group.

4. The method according to claim 1, wherein the binding site is located in the cell lumen, in the cytoplasm, in the cell wall, or/and in a secreted protein.

5. The method according to claim 1, wherein the antibiotic is a beta-lactam antibiotic.

6. The method according to claim 5, wherein the beta-lactam antibiotic binds to the Penicillin Binding Protein 2.

7. The method according to claim 1, wherein the label in step (c) is detected via epifluorescence microscopy, flow cytometry, laser scanning devices, time resolved fluorometry, luminescence detection, isotope detection, hyper spectral imaging scanner, Surface Plasmon Resonance or another evanescence based reading technology.

8. The method according to claim 1, wherein the microorganism is identified in the biological sample.

9. The method according to claim 8, wherein the microorganism is identified in step (d) by using a labelled nucleic acid capable of specifically hybridizing with a nucleic acid in the micro-organism under in-situ conditions.

10. Method according to claim 8, wherein the microorganism is identified in step (d) by fluorescence in situ hybridization (FISH).

11. The method according to claim 8, wherein the identification of the micro-organism and the detection of the labelled antibiotic in the micro-organism are run concurrently.

12. The method according to claim 8, wherein the micro-organism is identified in step (d) using epifluorescence microscopy, flow cytometry, laser scanning devices, time resolved fluorometry, luminescence detection, isotope detection, hyper spectral imaging scanner, Surface Plasmon Resonance or another evanescence based reading technology.

13. The method according to claim 1, wherein said micro-organism is selected from the group consisting of bacteria, yeasts and molds.

14. The method of claim 1, wherein the micro-organism is a gram positive bacterium which is perforated by using a gram Positive Perforation Buffer containing saponin, nisin, tris pH 8, lysozyme, lysostaphin and water.

15. The method according to claim 1, wherein the micro-organism is a yeasts or a mould, which is perforated by the formulation Yeast Perforation Buffer in Table 2.

16. The method according to claim 9, wherein said micro-organism is a Methicillin Resistant *Staphylococcus aureus* (MRSA) which is identified by in-situ hybridization simultaneously with the detection of the expression of the Penicillin Binding Protein 2 by binding a labelled β-Lactam antibiotic.

17. The method according to claim 9, wherein said micro-organism is a Methicillin Resistant *Staphylococcus aureus* (MRSA) which is identified by in-situ hybridization simultaneously with screening for resistance to Clindamycin or Trimethoprim sulfa.

18. The method according to claim 9, wherein a Vancomycin Resistant *Staphylococcus aureus* (VRSA) is identified by in-situ hybridisation simultaneously with the ability to bind labelled Vancomycin.

19. The method according to claim 9, wherein a Vancomycin Resistant *Staphylococcus* (VRS) is identified by in-situ hybridisation simultaneously with the ability to bind labelled Vancomycin.

20. The method according to claim 9, wherein a Vancomycin Resistant Enterococci (VRE) is identified by in-situ hybridisation simultaneously with the ability to bind labelled Vancomycin.

21. The method according to claim 8, wherein a resistance towards β-lactam antibiotics due to the secretion of β-lactamase (ESBL) is detected by the revealing of the presence of said β-lactamase by the binding of labelled clavulanic acid together with the identification of gram negative micro-organisms.

22. The method according to claim 8, wherein a resistance towards β-lactam antibiotics due to the secretion of metalo-β-lactamases (MBL) is detected by the revealing of the presence of said β-lactamase by the binding of labelled imipenem together with the identification of gram negative micro-organisms.

23. The method according to claim 8, wherein a resistance to macrolides, lincosamide and streptogramin (MLS) is detected via the binding of labelled erythromycin or/and Clindamycin together with the identification of Streptococci.

24. The method according to claim 8, wherein a drug resistant *Streptococcus pneumoniae* (DRSP) is identified with FSH together with the respective resistance towards beta-lactams and macrolides.

25. The method according to claim 8, wherein high level Aminoglycoside resistant Enterococci (HLAR) are detected via FSH and labelled Gentamycin.

26. The method of claim 1 which is a diagnostic method.

27. The method according to claim 3, wherein the antibiotic is labelled by a fluorescent labelling group.

28. The method according to claim 13, wherein said bacteria is a gram positive or gram negative bacteria.

* * * * *